United States Patent
Matsuyama et al.

(10) Patent No.: US 10,651,390 B2
(45) Date of Patent: May 12, 2020

(54) TERTIARY AMINE COMPOUND, PHOTOELECTRIC CONVERSION ELEMENT, AND SOLAR CELL

(71) Applicant: RICOH COMPANY, LTD., Tokyo (JP)

(72) Inventors: Tsuyoshi Matsuyama, Shizuoka (JP); Yuuji Tanaka, Shizuoka (JP); Ryota Arai, Shizuoka (JP); Tokushige Kino, Shizuoka (JP); Naomichi Kanei, Shizuoka (JP); Tamotsu Horiuchi, Shizuoka (JP)

(73) Assignee: RICOH COMPANY, LTD., Tokyo (JP)

( * ) Notice: Subject to any disclaimer, the term of this patent is extended or adjusted under 35 U.S.C. 154(b) by 146 days.

(21) Appl. No.: 15/617,070

(22) Filed: Jun. 8, 2017

(65) Prior Publication Data

US 2017/0358399 A1    Dec. 14, 2017

(30) Foreign Application Priority Data

Jun. 8, 2016   (JP) .................................. 2016-114029
May 23, 2017   (JP) .................................. 2017-101969

(51) Int. Cl.
*H01L 51/00* (2006.01)
*C07D 213/38* (2006.01)
*H01L 51/42* (2006.01)

(52) U.S. Cl.
CPC ........ *H01L 51/0061* (2013.01); *C07D 213/38* (2013.01); *H01L 51/0032* (2013.01);
(Continued)

(58) Field of Classification Search
CPC .............. H01L 51/4213; H01L 51/442; H01L 51/0077; H01L 51/0061; H01L 51/0067;
(Continued)

(56) References Cited

U.S. PATENT DOCUMENTS 3,542,547 A    11/1970 Wilson
3,824,099 A     7/1974 Champ et al.
(Continued)

FOREIGN PATENT DOCUMENTS

JP   34-005466   6/1959
JP   45-000555   1/1970
(Continued)

OTHER PUBLICATIONS

Ikeda et al, Construction of an M3L2A6 Cage with Small Windows from a Flexible Tripodal Ligand and Cu(hfac)3 (Year: 2013).*
(Continued)

*Primary Examiner* — Uyen M Tran
(74) *Attorney, Agent, or Firm* — Oblon, McClelland, Maier & Neustadt, L.L.P.

(57) ABSTRACT

A tertiary amine compound is provided. The tertiary amine compound is represented by the following general formula (1):

General Formula (1)

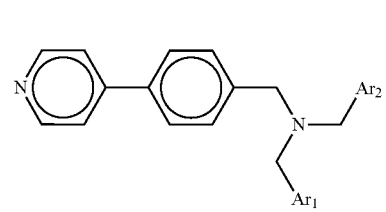

where each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring.

9 Claims, 2 Drawing Sheets

(52) U.S. Cl.
CPC ...... *H01L 51/0086* (2013.01); *H01L 51/4226* (2013.01); *Y02E 10/542* (2013.01); *Y02E 10/549* (2013.01)

(58) Field of Classification Search
CPC ............. H01L 51/0071; H01L 51/0035; H01L 51/0037; H01G 9/2009; H01G 9/2059
See application file for complete search history.

(56) References Cited

U.S. PATENT DOCUMENTS

| | | | |
|---|---|---|---|
| 4,123,269 | A | 10/1978 | Von Hoene et al. |
| 4,150,987 | A | 4/1979 | Anderson et al. |
| 2014/0264184 | A1 | 9/2014 | Arai et al. |
| 2015/0041724 | A1 | 2/2015 | Arai et al. |
| 2015/0083210 | A1 | 3/2015 | Arai et al. |
| 2015/0083226 | A1 | 3/2015 | Arai et al. |
| 2015/0158814 | A1 | 6/2015 | Yanagawa et al. |
| 2015/0279573 | A1 | 10/2015 | Horiuchi et al. |
| 2015/0280142 | A1 | 10/2015 | Arai et al. |
| 2016/0126021 | A1 | 5/2016 | Tanaka et al. |
| 2016/0260912 | A1 | 9/2016 | Arai et al. |
| 2016/0276609 | A1 | 9/2016 | Horiuchi et al. |

FOREIGN PATENT DOCUMENTS

| | | |
|---|---|---|
| JP | 49-105536 | 10/1974 |
| JP | 54-058445 | 5/1979 |
| JP | 54-059143 | 5/1979 |
| JP | 56-123544 | 9/1981 |
| JP | 58-065440 | 4/1983 |
| JP | 60-098437 | 6/1985 |
| JP | 7-500630 | 1/1995 |
| JP | 9-199744 | 7/1997 |
| JP | 10-092477 | 4/1998 |
| JP | 10-093118 | 4/1998 |
| JP | 10-233238 | 9/1998 |
| JP | 11-086916 | 3/1999 |
| JP | 11-144773 | 5/1999 |
| JP | 11-204821 | 7/1999 |
| JP | 11-214730 | 8/1999 |
| JP | 11-214731 | 8/1999 |
| JP | 11-238905 | 8/1999 |
| JP | 11-265738 | 9/1999 |
| JP | 11-273754 | 10/1999 |
| JP | 11-273755 | 10/1999 |
| JP | 2000-026487 | 1/2000 |
| JP | 2000-106224 | 4/2000 |
| JP | 2000-323191 | 11/2000 |
| JP | 2001-052766 | 2/2001 |
| JP | 2001-059062 | 3/2001 |
| JP | 2001-076773 | 3/2001 |
| JP | 2001-076775 | 3/2001 |
| JP | 2002-164089 | 6/2002 |
| JP | 2003-007359 | 1/2003 |
| JP | 2003-007360 | 1/2003 |
| JP | 2003-031273 | 1/2003 |
| JP | 2003-264010 | 9/2003 |
| JP | 2004-063274 | 2/2004 |
| JP | 2004-095450 | 3/2004 |
| JP | 2004-115636 | 4/2004 |
| JP | 2004-200068 | 7/2004 |
| JP | 2004-235052 | 8/2004 |
| JP | 2006-032260 | 2/2006 |
| JP | 2015-128136 | 7/2015 |
| WO | WO94/004497 A1 | 3/1994 |

OTHER PUBLICATIONS

Jiang et al , Lewis acid-catalyzed redox-neutral amination of 2-(3-pyrroline-1-yl)benzaldehydes via intramolecular [1,5]-hydride shift/isomerization reaction (Year: 2014).*
STN search (Year: 2019).*
Stic search (Year: 2019).*
Scifinder search (Year: 2019).*
Tadas Malinauskas, et al., "Enhancing Thermal Stability and Lifetime of Solid-State Dye-Sensitized Solar Cells via Molecular Engineering of the Hole-Transporting Material Spiro-OMeTAD" ACS Appl. Mater. Interfaces, 2015, 7 (21), pp. 11107-11116.
Paidi Yella Reddy,et al., "Efficient Sensitization of Nanocrystalline TiO2 Films by a Near-IR-Absorbing Unsymmetrical Zinc Phthalocyanine" Angew. Chem. Int. Ed. 2007, 46, 373-376.
Daibin Kuang,et al., "Organic Dye-Sensitized Ionic Liquid Based Solar Cells: Remarkable Enhancement in Performance through Molecular Design of Indoline Sensitizers" Angew. Chem. Int. Ed. 2008, 47, 1923-1927.
Suyoung Hwang,et al., "A highly efficient organic sensitizer for dye-sensitized solar cells" Chem. Commun., 2007,4887-4489.
Tingli Ma, et al., "Photoelectrochemical properties of TiO2 electrodes sensitized by porphyrin derivatives with different numbers of carboxyl groups" Journal of Electroanalytical Chemistry 537(2002) 31-38.
K. Okada, et al., "Dye-sensitized Solar Cells for Energy Harvesting Device" Fujikura technical journal, 121 (2011) 42.
Pierre Bonhôte,et al., "Hydrophobic, Highly Conductive Ambient-Temperature Molten Salts" Inorg. Chem., 1996, 35, pp. 1168-1178.
Christophe Desmarets, et al., "Nickel(0)/Dihydroimidazol-2-ylidene Complex Catalyzed Coupling of Aryl Chlorides and Amines" J. Org. Chem., 2002, 67, pp. 3029-3036.
Julian Burschka,et al., "Tris(2-(1H-pyrazol-1-yl)pyridine)cobalt(III) as p-Type Dopant for Organic Semiconductors and Its Application in Highly Efficient Solid-State Dye-Sensitized Solar Cells" J. Am. Chem. Soc., 2011, 133, pp. 18042-18045.
Lei Yang, et al., "Initial Light Soaking Treatment Enables Hole Transport Material to Outperform Spiro-OMeTAD in Solid-State Dye-Sensitized Solar Cells" J. Am. Chem. Soc., 2013, 135, pp. 7378-7385.
Tamotsu Horiuchi, et al., "High Efficiency of Dye-Sensitized Solar Cells Based on Metal-Free Indoline Dyes" J. Am. Chem. Soc., 2004, 126, pp. 12218-12219.
Nagatoshi Koumura, et al., "Alkyl-Functionalized Organic Dyes for Efficient Molecular Photovoltaics" J. Am. Chem. Soc., 2006, 128, pp. 14256-14257.
Sanghoon Kim, et al., "Molecular Engineering of Organic Sensitizers for Solar Cell Applications" J. Am. Chem. Soc., 2006, 128, pp. 16701-16707.
K. Kalyanasundaram, et al., "Sensitization of titanium dioxide in the visible light region using zinc porphyrins" J. Phys. Chem., 1987, 91, pp. 2342-2347.
Andreas Kay, et al., "Artificial photosynthesis. 1. Photosensitization of titania solar cells with chlorophyll derivatives and related natural porphyrins" J. Phys. Chem., 1993, 97, pp. 6272-6277.
Zhong-Sheng Wang, et al., "Thiophene-Functionalized Coumarin Dye for Efficient Dye-Sensitized Solar Cells: Electron Lifetime Improved by Coadsorption of Deoxycholic Acid" J. Phys. Chem. C, 2007, 111, pp. 7224-7230.
Md. K. Nazeeruddin, et al., "Efficient Near-IR Sensitization of Nanocrystalline TiO2 Films by Zinc and Aluminum Phthalocyanines" J. Porphyrins Phthalocyanines 3, 230-237(1999).
Haim Tsubery, et al., "Biochemical Assays of Immobilized Oligonucleotides with Mass Spectrometry" Langmuir, 2008, 24, pp. 5433-5438.
Takashi Sekiguchi, et al., "improvement of Durability of Dye-Sensitized Solar Cells for Indoor Applications" Panasonic Electric Works technical report, 56 (2008) 87.

* cited by examiner

TERTIARY AMINE COMPOUND, PHOTOELECTRIC CONVERSION ELEMENT, AND SOLAR CELL

CROSS-REFERENCE TO RELATED APPLICATIONS

This patent application is based on and claims priority pursuant to 35 U.S.C. § 119(a) to Japanese Patent Application Nos. 2016-114029 and 2017-101969, filed on Jun. 8, 2016 and May 23, 2017, respectively, in the Japan Patent Office, the entire disclosure of each of which is hereby incorporated by reference herein.

BACKGROUND

Technical Field

The present disclosure relates to a tertiary amine compound, a photoelectric conversion element, and a solar cell.

Description of the Related Art

Electronic circuits became able to be driven with very small electric power lately. For example, various electronic parts, such as sensors, can be driven with very small electric power. In particular, environmental power generating elements that generate and consume power on the spot are expected as stand-alone power sources for driving sensors. Among environmental power generating elements, solar cells that can generate power wherever light exists are attracting attention.

As one type of solar cells, solid-type photoelectric conversion elements have been proposed. It has been reported that they can generate power from pseudo sunlight, however, never generate power from room light. In most known solar cells, the cathode was made of a silver or gold film formed by a dry film-forming process, which is more expensive than that formed by a wet film-forming process. In order to reduce the cost, wet film formation processes are preferred. However, the wet film-forming processes may cause a problem that an organic solvent generally used therein dissolves the hole transport layer. To solve this problem, an aqueous paste of a polythiophene derivative (e.g., PEDOT/PSS) has been preferably used to form the film. On the other hand, it is generally known that residual moisture in the film deteriorates the performance of the resulting solar cell. Thus, the film needs to be heated to 100° C. or higher so that moisture is removed therefrom. In particular, to acquire reliable durability, it is preferred that the film is heated to 120° C. or higher. However, such heating significantly degrades the performance of the solar cell. Therefore, it has not been reported any high-power solid-type dye sensitized solar cell.

SUMMARY

In accordance with some embodiments of the present invention, a tertiary amine compound is provided. The tertiary amine compound is represented by the following general formula (1):

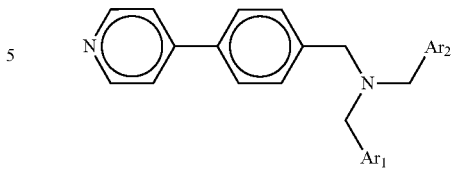

General Formula (1)

where each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring.

In accordance with some embodiments of the present invention, a photoelectric conversion element is provided. The photoelectric conversion element includes a first electrode, a hole blocking layer containing the above tertiary amine compound, an electron transport layer, a hole transport layer, and a second electrode.

In accordance with some embodiments of the present invention, another photoelectric conversion element is provided. The photoelectric conversion element includes a transparent conductive film substrate, a first electrode overlying the transparent conductive film substrate, a hole blocking layer overlying the first electrode, an electron transport layer overlying the hole blocking layer, an organic-inorganic perovskite compound layer overlying the electron transport layer, a hole transport layer overlying the organic-inorganic perovskite compound layer, containing the above tertiary amine compound, and a second electrode overlying the hole transport layer.

In accordance with some embodiments of the present invention, a solar cell including one of the above photoelectric conversion elements is provided.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

Figure 1:
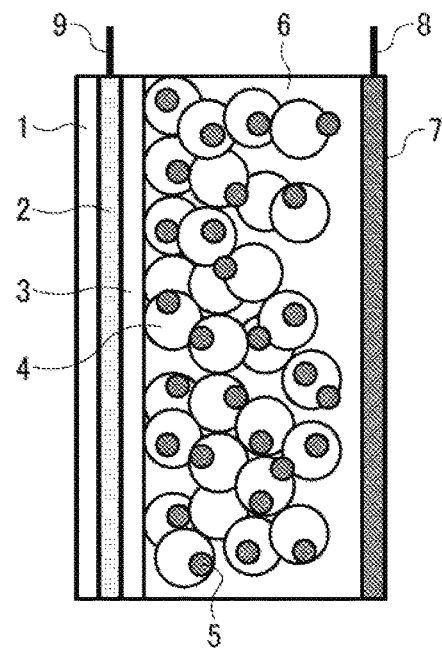
FIG. 1 is a cross-sectional view of a photoelectric conversion element according to an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

Within the context of the present disclosure, if a first layer is stated to be "overlaid" on, or "overlying" a second layer, the first layer may be in direct contact with a portion or all of the second layer, or there may be one or more intervening layers between the first and second layer, with the second layer being closer to the substrate than the first layer.

One object of the present invention is to provide a tertiary amine compound for use in a photoelectric conversion element that exhibits excellent photoelectric conversion characteristics under weak emission light, such as indoor light, even after being exposed to a high-temperature process.

In accordance with some embodiments of the present invention, a photoelectric conversion element is provided that exhibits excellent photoelectric conversion characteristics under weak emission light, such as indoor light, even after being exposed to a high-temperature process, by containing a specific tertiary amine compound in a hole transport layer of the photoelectric conversion element.

The tertiary amine compound according to an embodiment of the present invention is represented by the following general formula (1).

General Formula (1)

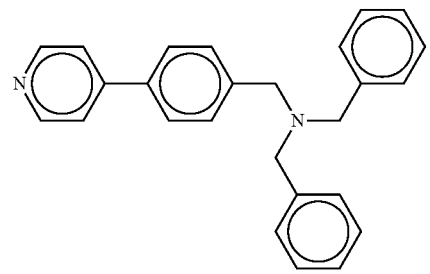

where each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring. The alkyl group and the alkoxy group may have a substituent. $Ar_1$ and $Ar_2$ may be either the same or different.

Preferably, the alkyl group is an alkyl group having 1 to 4 carbon atoms, and the alkoxy group is methoxy group or ethoxy group.

When the tertiary amine compound is contained in a hole transport layer of a photoelectric conversion element and the photoelectric conversion element is exposed to a high-temperature process, the photoelectric conversion element exhibits excellent photoelectric conversion characteristics. It has been confirmed that such a photoelectric conversion element has a distinctive advantage in performing photoelectric conversion under weak light, such as indoor light.

Specific examples of the compound represented by the general formula (1) include, but are not limited to, the following compounds No. 1-1 to 1-8.

Compound No. 1-1

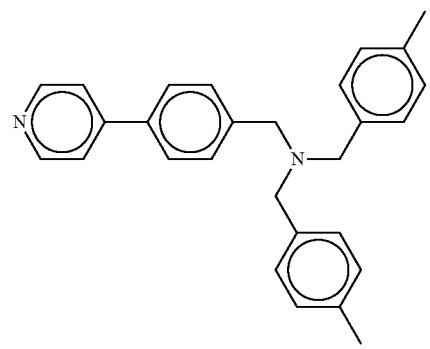

Compound No. 1-2

Compound No. 1-3

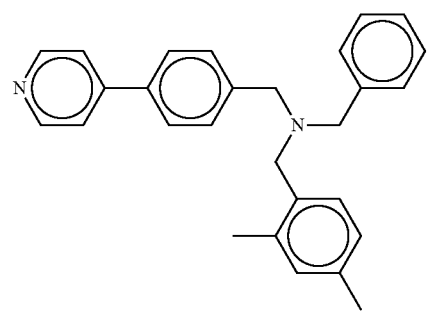

Compound No. 1-4

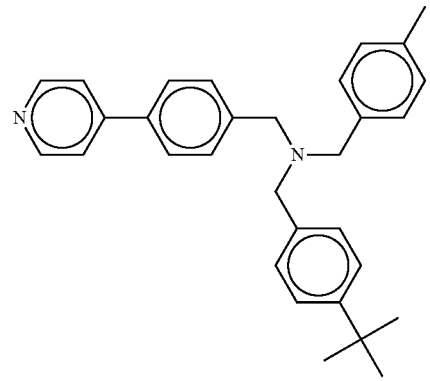

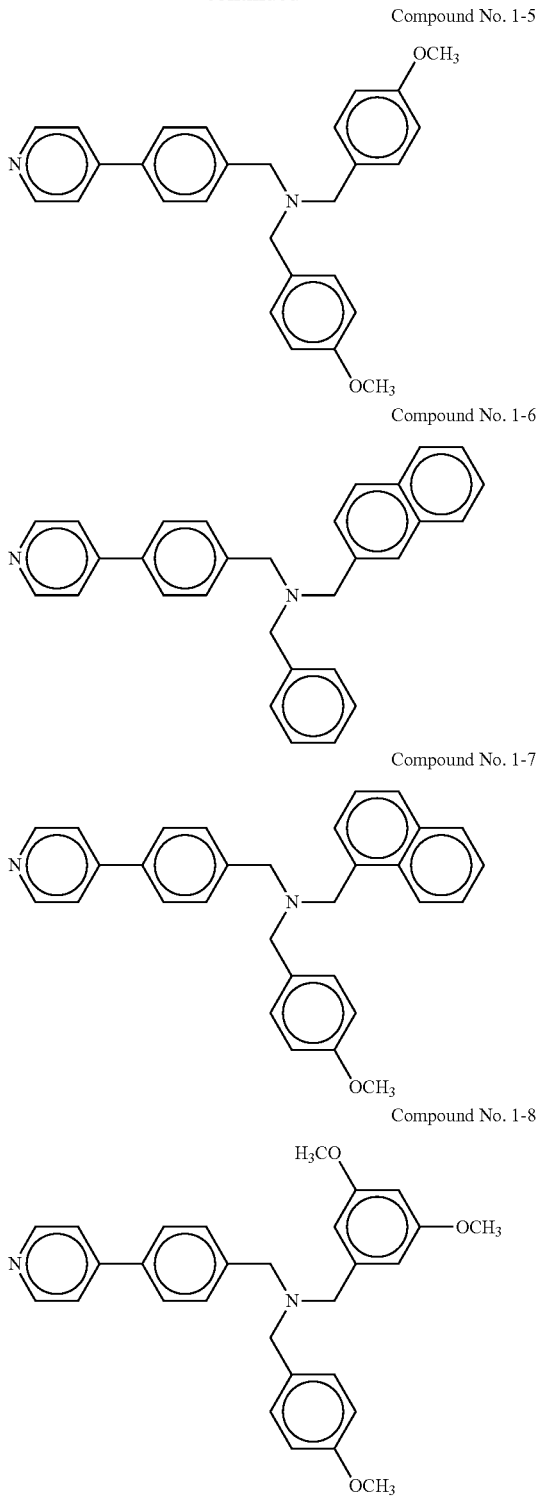

Compound No. 1-5

Compound No. 1-6

Compound No. 1-7

Compound No. 1-8

The photoelectric conversion element according to a first embodiment of the present invention includes a first electrode, a hole blocking layer, an electron transport layer, a hole transport layer, and a second electrode. The hole transport layer contains the tertiary amine compound according to an embodiment of the present invention.

A configuration of this photoelectric conversion element is described below with reference to FIG. 1. FIG. 1 is a cross-sectional view of a photoelectric conversion element according to the first embodiment of the present invention.

Referring to FIG. 1, a first electrode 2 is formed on a substrate 1. A hole blocking layer 3 is formed on the first electrode 2. A porous electron transport layer 4 is formed on the hole blocking layer 3. The porous electron transport layer 4 contains an electron transport material to which a photosensitizing material 5 is adsorbed. A second electrode 7 is disposed facing the first electrode 2, and a hole transport layer 6 is disposed therebetween. In addition, lead lines 8 and 9 are disposed to electrically connect the first electrode 2 and the second electrode 7 to each other.

Substrate

The substrate 1 is not limited to any particular material. Preferably, the substrate 1 is made of a transparent material, such as a glass plate, a transparent plastic plate, a transparent plastic film, and an inorganic transparent crystalline body.

First Electrode

The first electrode 2 is made of a visible-light-transmissive conductive material. For example, visible-light-transmissive conductive materials generally used for photoelectric conversion elements and liquid crystal panels may be used.

Specific examples of such materials used for the first electrode include, but are not limited to, indium-tin oxide (ITO), fluorine-doped tin oxide (FTO), antimony-doped tin oxide (ATO), indium-zinc oxide, niobium-titanium oxide, and graphene. Each of these substances can be used alone to form a single layer or in combination with others to form a multilayer.

Preferably, the first electrode has a thickness of from 5 nm to 10 μm, and more preferably from 50 nm to 1 μm.

To maintain a constant level of rigidity, the first electrode 2 is preferably formed on the substrate 1 made of a visible-light-transmissive material such as a glass plate, a transparent plastic plate, a transparent plastic film, and an inorganic transparent crystalline body.

A combined body of the first electrode 2 and the substrate 1 may also be used. Examples of such a combined body include, but are not limited to, an FTO-coated glass plate, an ITO-coated glass plate, a zinc-oxide-and-aluminum-coated glass plate, an FTO-coated transparent plastic film, and an ITO-coated transparent plastic film.

In addition, a combined body of a substrate (such as glass substrate) with a transparent electrode made of tin oxide or indium oxide doped with a cation or anion having a different atomic valence, or with a metallic electrode having a mesh-like or stripe-like structure to be light transmissive, can also be used.

Each of these materials can be used alone, or mixed with or laminated on the others. For the purpose of reducing resistance, metallic lead wires may be used in combination.

The metallic lead wire may be made of aluminum, copper, silver, gold, platinum, or nickel. The metallic lead wire may be disposed on the substrate by means of vapor deposition, sputtering, or pressure bonding, and ITO or FTO may be further disposed thereon.

Hole Blocking Layer

The hole blocking layer 3 is made of a visible-light-transmissive material having electron transportability. Preferred examples of such a material include titanium oxide. The hole blocking layer is provided for suppressing electric power reduction that may be caused when a hole in an electrolyte and an electron on a surface of an electrode are recombined (i.e., reverse electron transfer occurs) as the electrolyte comes into contact with the electrode. The effect of the hole blocking layer 3 is remarkably exerted in a solid-type dye sensitized solar cell. This is because, in solid-type dye sensitized solar cells generally containing organic hole transport materials, the recombination (reverse electron transfer) speed of a hole in the hole transport material with an electron on a surface of the electrode is greater than that in wet-type dye sensitized solar cells containing electrolytic solutions.

The method for forming the hole blocking layer is not particularly limited. Preferably, the hole blocking layer is formed by a method that can impart a high internal resistance, so that the resulting hole blocking layer can suppress current loss under indoor light. Generally, the hole blocking layer can be formed by a sol-gel method that is one of wet film-forming methods. However, the film formed by this method cannot sufficiently suppress current loss because the film density is too low. On the other hand, the film formed by sputtering, that is one of dry film-forming methods, can sufficiently suppress current loss since the film density is high enough.

The hole blocking layer has another function of preventing the first electrode 2 and the hole transport layer 6 from electrically contacting with each other. Preferably, the thickness of the hole blocking layer is in the range of from 5 nm to 1 μm, but is not limited thereto. When the hole blocking layer is formed by a wet film-forming method, preferably, the thickness is in the range of from 500 to 700 nm. When the hole blocking layer is formed by a dry film-forming method, preferably, the thickness is in the range of from 10 to 30 nm.

Electron Transport Layer

In the photoelectric conversion element according to an embodiment of the present invention, the porous electron transport layer 4 is formed on the hole blocking layer 3. The electron transport layer 4 may be either single-layered or multi-layered.

The electron transport layer 4 comprises an electron transport material. Preferred examples of the electron transport material include semiconductive particles.

A multi-layered electron transport layer can be formed by multiply applying dispersion liquids of semiconductor particles different in particle diameter, or multiply applying different types of semiconductors and/or compositions containing different type of resins and additives.

Such multiple application is effective when the layer formed by a single application is insufficient in thickness.

Generally, as the thickness of the electron transport layer increases, the light capture rate increases, because the amount of photosensitizing materials carried per unit projected area increases. However, at the same time, the diffusion distance of injected electrons also increases to increase loss due to recombination of charge.

Accordingly, the electron transport layer preferably has a thickness of from 100 nm to 100 μm.

The semiconductor is not limited to any particular material.

Specific examples of the semiconductor include, but are not limited to, single-body semiconductors such as silicon and germanium, compound semiconductors such as metal chalcogenides, and compounds having a perovskite structure.

Specific examples of the metal chalcogenides include, but are not limited to, oxides of titanium, tin, zinc, iron, tungsten, zirconium, hafnium, strontium, indium, cerium, yttrium, lanthanum, vanadium, niobium, and tantalum; sulfides of cadmium, zinc, lead, silver, antimony, and bismuth; selenides of cadmium and lead; and tellurides of cadmium.

Specific examples of the compound semiconductors include, but are not limited to, phosphides of zinc, gallium, indium, and cadmium; gallium arsenide; copper-indium selenide; and copper-indium sulfide.

Specific examples of the compounds having a perovskite structure include, but are not limited to, strontium titanate, calcium titanate, sodium titanate, barium titanate, and potassium niobate.

Among these materials, oxide semiconductors are preferable, and titanium oxide, zinc oxide, tin oxide, and niobium oxide are more preferable. Each of these materials can be used alone or in combination with others. The semiconductor is not limited in crystal type and may be either single crystalline, polycrystalline, or amorphous.

The semiconductor particles are not limited in size. Preferably, the average particle diameter of the primary particle thereof is in the range of from 1 to 100 nm, more preferably from 5 to 50 nm.

It is possible to further improve efficiency by mixing or stacking another type of semiconductor particle having a greater average particle diameter so that the resulting layer scatters incident light. In this case, the semiconductor particle preferably has an average particle diameter of from 50 to 500 nm.

The electron transport layer is not limited in its formation method and can be formed by, for example, a vacuum film-forming method, such as sputtering, or a wet film-forming method.

In view of production cost, wet film-forming methods are preferable. Specifically, a method in which a paste dispersing a powder or sol of semiconductor particles is applied to an electron collecting electrode substrate is preferable.

In this wet film-forming method, how to apply the paste is not particularly limited.

For example, the paste may be applied by means of dipping, spraying, wire bar, spin coating, roller coating, blade coating, gravure coating, or wet printing such as relief, offset, gravure, intaglio, rubber plate, and screen printings.

A dispersion liquid of semiconductor particles may be prepared by means of mechanical pulverization or mill, specifically by dispersing at least the semiconductor particles alone or a mixture of the semiconductor particles with a resin in water or an organic solvent.

Specific examples of the resin mixed with the semiconductor particles include, but are not limited to, homopolymers and copolymers of vinyl compounds such as styrene, vinyl acetate, acrylate, and methacrylate; and silicone resin, phenoxy resin, polysulfone resin, polyvinyl butyral resin, polyvinyl formal resin, polyester resin, cellulose ester resin, cellulose ether resin, urethane resin, phenol resin, epoxy resin, polycarbonate resin, polyarylate resin, polyamide resin, and polyimide resin.

Specific examples of solvents for dispersing the semiconductor particles include, but are not limited to, water; alcohol solvents such as methanol, ethanol, isopropyl alcohol, and α-terpineol; ketone solvents such as acetone, methyl ethyl ketone, and methyl isobutyl ketone; ester solvents such as ethyl formate, ethyl acetate, n-butyl acetate; ether solvents such as diethyl ether, dimethoxyethane, tetrahydrofuran, dioxolan, and dioxane; amide solvents such as N,N-dimethylformamide, N,N-dimethylacetamide, and N-methyl-2-pyrrolidone; halogenated hydrocarbon solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene. These solvents can be used alone or in combination with others as a mixed solvent.

To prevent reaggregation of the semiconductor particles in a dispersion liquid or a paste obtained by a sol-gel method, etc., an acid (e.g., hydrochloric acid, nitric acid, acetic acid), a surfactant (e.g., polyoxyethylene(10) octyl phenyl ether), or a chelator (e.g., acetyl acetone, 2-aminoethanol, ethylenediamine) can be added thereto.

To improve film-forming performance, a thickener can also be added thereto.

Specific examples of the thickener include, but are not limited to, polymers such as polyethylene glycol and polyvinyl alcohol, and ethyl cellulose.

It is preferable that semiconductor particles having been applied are brought into electronic contact with each other and exposed to burning, microwave irradiation, electron beam irradiation, or laser light irradiation, for increasing the film strength and adhesion to the substrate. Each of these treatments can be conducted alone or in combination with others.

In the burning, the burning temperature is preferably in the range of from 30° C. to 700° C., more preferably from 100° C. to 600° C., but is not limited thereto. When the burning temperature is excessively raised, the resistance of the substrate may become too high or the substrate may melt. The burning time is preferably from 10 minutes to 10 hours, but is not limited thereto.

In the microwave irradiation, the electron transport layer may be irradiated from either the layer-formed side or the opposite side thereof.

The irradiation time is preferably within 1 hour, but is not limited thereto.

After the burning, for the purpose of increasing the surface area of the semiconductor particles as well as increasing the efficiency of electron injection from the photosensitizing compound to the semiconductor particles, a chemical plating treatment using an aqueous solution of titanium tetrachloride or a mixed solution thereof with an organic solvent, or an electrochemical plating treatment using an aqueous solution of titanium trichloride may be conducted.

A layer in which semiconductor particles having a diameter of several tens nanometers are stacked by sintering, etc., forms a porous structure. Such a nano porous structure has a very large surface area. The surface area can be represented by a roughness factor.

The roughness factor is a numerical value indicating the ratio of the actual area of the inside of the porous structure to the surface area of the semiconductor particles applied to the substrate. Accordingly, the higher the roughness factor, the better. In connection with the thickness of the electron transport layer, the roughness factor is preferably 20 or more.

Photosensitizing Material

For more improving conversion efficiency, preferably, the photosensitizing material 5 is adsorbed to the surface of the electron transport material constituting the porous electron transport layer 4.

The photosensitizing material 5 is not limited to any particular material so long as it can be photoexcited. Specific examples of such compounds include, but are not limited to, the following compounds: metal complex compounds described in JP-07-500630-A, JP-10-233238-A, JP-2000-26487-A, JP-2000-323191-A, and JP-2001-59062; coumarin compounds described in JP-10-93118-A, JP-2002-164089-A, JP-2004-95450-A, and *J. Phys. Chem. C.,* 7224, Vol. 111 (2007); polyene compounds described in JP-2004-95450 and *Chem. Commun.,* 4887 (2007); indoline compounds described in JP-2003-264010-A, JP-2004-63274-A, JP-2004-115636-A, JP-2004-200068-A, JP-2004-235052-A, J. Am. Chem. Soc., 12218, Vol. 126 (2004), and *Angew. Chem. Int. Ed.,* 1923, Vol. 47 (2008); thiophene compounds described in *J. Am. Chem. Soc.,* 16701, Vol. 128 (2006) and *J. Am. Chem. Soc.,* 14256, Vol. 128 (2006); cyanine dyes described in JP-11-86916-A, JP-11-214730-A, JP-2000-106224-A, JP-2001-76773-A, and JP-2003-7359-A; merocyanine dyes described in JP-11-214731-A, JP-11-238905-A, JP-2001-52766-A, JP-2001-76775-A, and JP-2003-7360-A; 9-aryl xanthene compounds described in JP-10-92477-A, JP-11-273754-A, JP-11-273755-A, and JP-2003-31273-A; triarylmethane compounds described in JP-10-93118-A and JP-2003-31273-A; and phthalocyanine compounds and porphyrin compounds described in JP-09-199744-A, JP-10-233238-A, JP-11-204821-A, JP-11-265738-A, J. Phys. Chem., 2342, Vol. 91 (1987), *J. Phys. Chem. B,* 6272, Viol. 97 (1993), *Electroanal. Chem.,* 31, Vol. 537 (2002), JP-2006-032260-A, *J. Porphyrins Phthalocyanines,* 230, Vol. 3 (1999), *Angew. Chem. Int. Ed.,* 373, Vol. 46 (2007), and *Langmuir,* 5436, Vol. 24 (2008). Among these compounds, metal complex compounds, coumarin compounds, polyene compounds, indoline compounds, and thiophene compounds are preferable.

Specific examples of the metal complex compounds include, but are not limited to, the following compounds (10) to (14). Specific examples of the coumarin compounds include, but are not limited to, the following compound (15). Specific examples of the polyene compounds include, but are not limited to, the following compound (16). Specific examples of the indoline compounds include, but are not limited to, the following compounds (17) to (19). Specific examples of the thiophene compounds include, but are not limited to, the following compound (20). In these compounds, each carboxylic group (—COOH) may form a salt with a quaternary alkylamine.

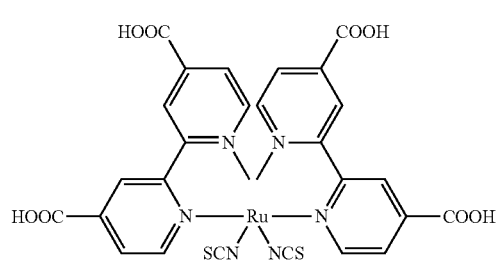

(10)

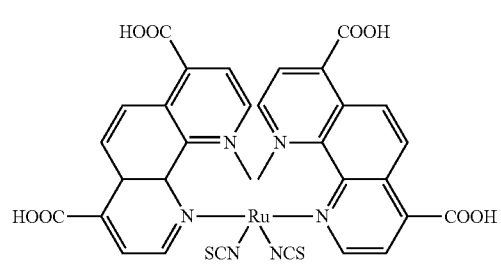

(11)

-continued
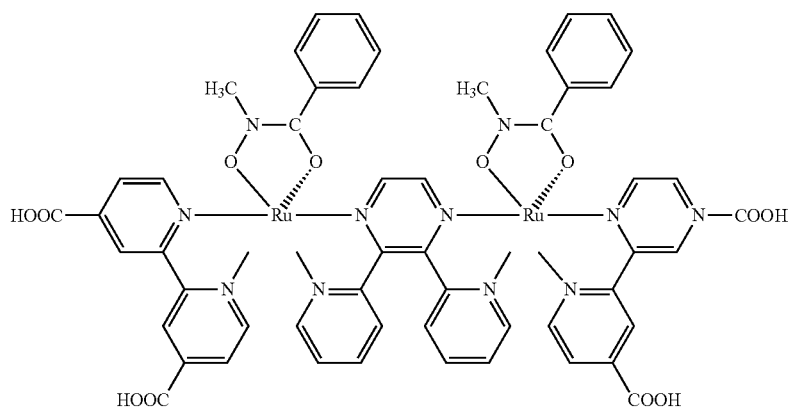
(12)
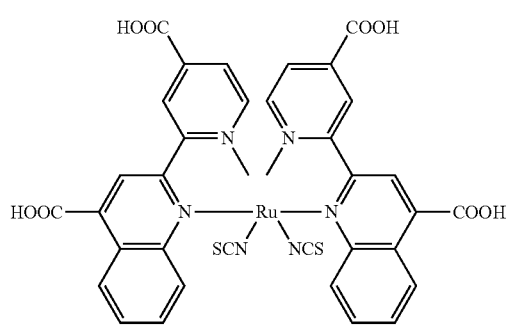
(13)
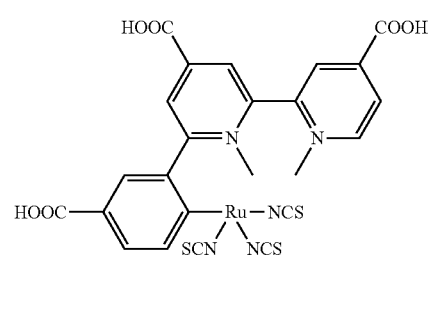
(14)
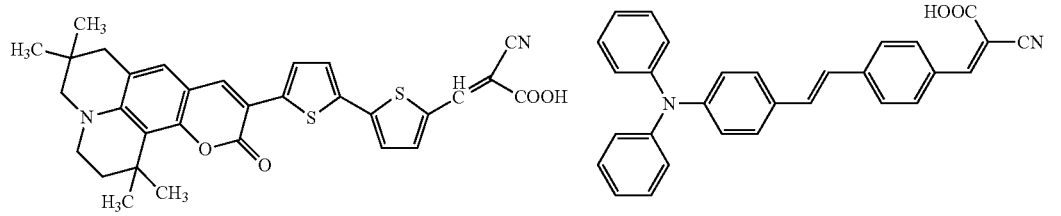
(15) (16)
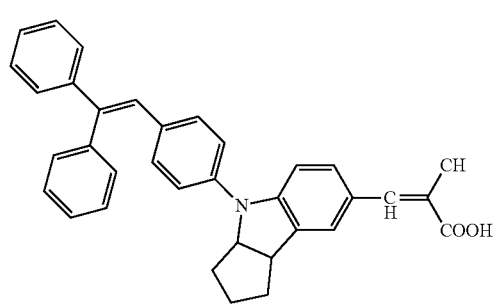
(17)
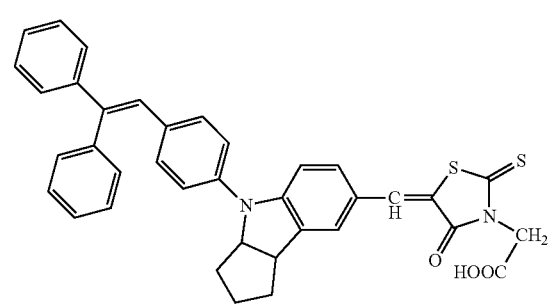
(18)
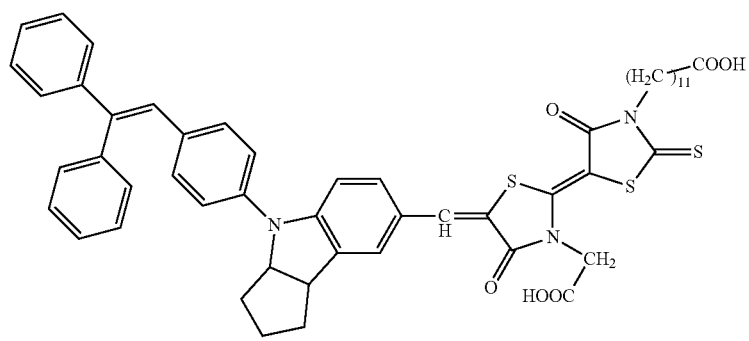
(19)

-continued
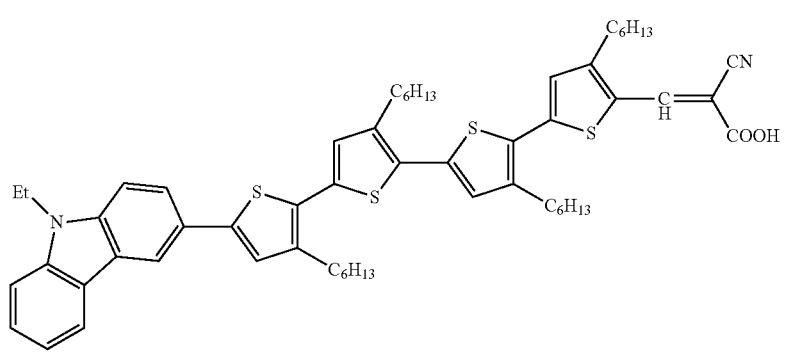
(20)
More specifically, the compounds D131, D102, and D358 available from Mitsubishi Paper Mills Limited, respectively represented by the following formulae (3), (4), and (5), are preferable.
(D131)
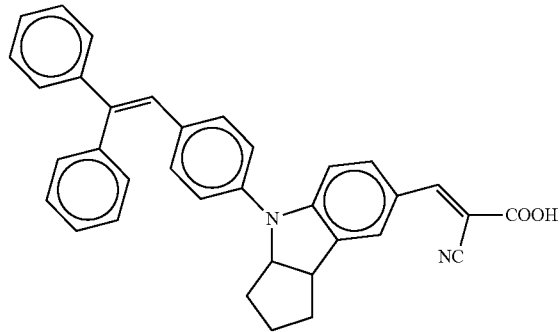
Formula (3)
(D102)
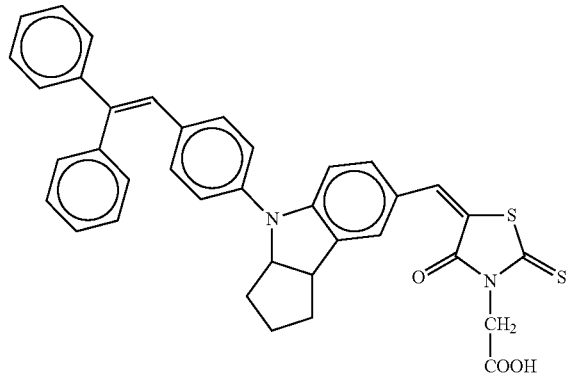
Formula (4)

(D358)

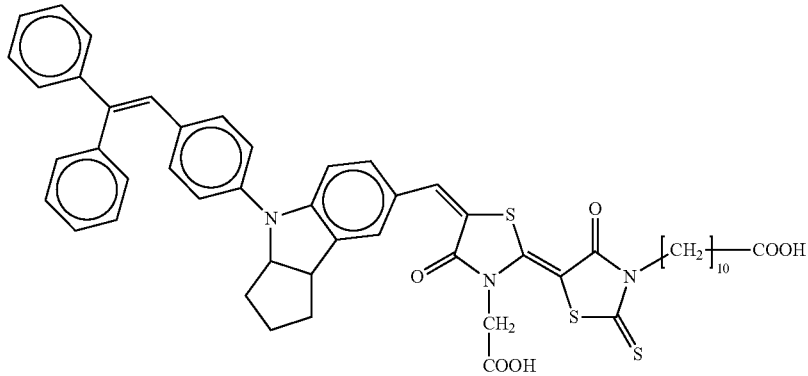

Formula (5)

The photosensitizing material 5 can be adsorbed to the electron transport material constituting the porous electron transport layer 4 by dipping the electron collecting electrode containing semiconductor particles in a solution or liquid dispersion of the photosensitizing material 5, or applying the solution or liquid dispersion of the photosensitizing material 5 to the porous electron transport layer 4.

In the former case, for example, an immersion method, a dipping method, a roller method, or an air knife method may be employed.

In the latter case, for example, a wire bar method, a slide hopper method, an extrusion method, a curtain method, a spin method, or a spray method may be employed.

Alternatively, the photosensitizing material 5 may be adsorbed to the electron transport material in a supercritical fluid such as carbon dioxide.

When adsorbing the photosensitizing material to the electron transport material, a condensation agent can be used in combination.

The condensation agent may act as a catalyst for physically or chemically binding the photosensitizing material and the electron transport material to a surface of an inorganic material, or may stoichiometrically act for advantageously transfer chemical equilibrium.

Further, a condensation auxiliary agent, such as a thiol and a hydroxy compound, may be used in combination.

Specific examples of solvents for dissolving or dispersing the photosensitizing material include, but are not limited to, water; alcohol solvents such as methanol, ethanol, and isopropyl alcohol; ketone solvents such as acetone, methyl ethyl ketone, and methyl isobutyl ketone; ester solvents such as ethyl formate, ethyl acetate, and n-butyl acetate; ether solvents such as diethyl ether, dimethoxyethane, tetrahydrofuran, dioxolan, and dioxane; amide solvents such as N,N-dimethylformamide, N,N-dimethylacetamide, and N-methyl-2-pyrrolidone; halogenated hydrocarbon solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene. These solvents can be used alone or in combination with others.

Some photosensitizing materials more effectively work when aggregation is suppressed. Therefore, an aggregation dissociating agent can be used in combination.

Specific preferred examples of the aggregation dissociating agent include, but are not limited to, steroid compounds such as cholic acid and chenodeoxycholic acid; long-chain alkylcarboxylic acids; and long-chain alkylsulfonic acids.

The addition amount of the aggregation dissociating agent is preferably in the range of from 0.01 to 500 parts by mass, more preferably from 0.1 to 100 parts by mass, based on 1 part of the photosensitizing material.

Preferably, the temperature at the adsorption of the photosensitizing material alone or a combination of the photosensitizing material and aggregation dissociating agent is in the range of from −50 to 200° C.

The adsorption may be performed under either static condition or stirring.

The stirring may be performed by, for example, a stirrer, a ball mill, a paint conditioner, a sand mill, an attritor, a disperser, or an ultrasonic disperser.

The time required for the adsorption is, preferably, in the range of from 5 seconds to 1,000 hours, more preferably from 10 seconds to 500 hours, and most preferably from 1 minute to 150 hours.

Preferably, the adsorption is performed in dark place.

Hole Transport Layer

Generally, a hole transport layer comprises an electrolytic solution in which a redox pair is dissolved in an organic solvent, a gel electrolyte in which an organic solvent solution of a redox pair is impregnated in a polymer matrix, a molten salt containing a redox pair, a solid electrolyte, an inorganic hole transport material, an organic hole transport material, etc. The hole transport layer 6 according to an embodiment of the present invention preferably contains an organic hole transport material represented by the following general formula (2).

General Formula (2)

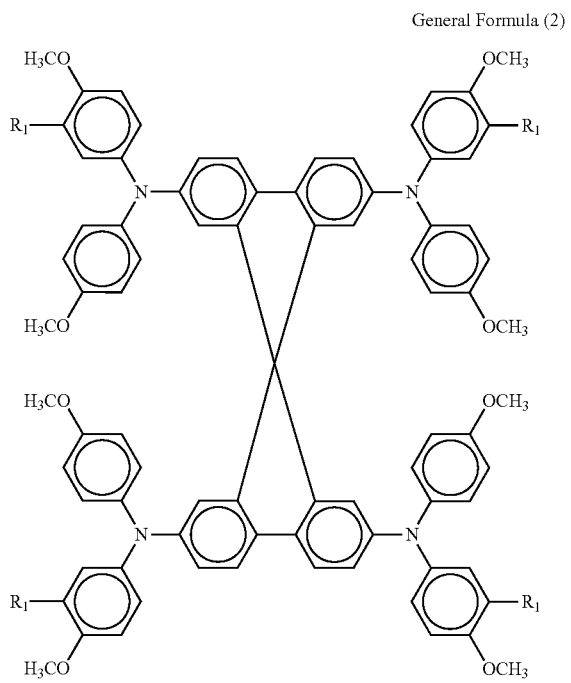

In the general formula (2), R₁ represents a hydrogen atom or methyl group.

The hole transport layer 6 may have either a single-layer structure or a multi-layer structure comprising multiple types of materials. In the case of multi-layer structure, it is preferable that a hole transport layer closest to the second electrode 7 contains a polymeric material.

Having high film-forming performance, the polymeric material can smoothen the surface of the porous electron transport layer, thereby improving photoelectric conversion characteristics.

In addition, having difficulty in permeating the porous electron transport layer, the polymeric material can also sufficiently cover the surface of the porous electron transport layer, thereby preventing the occurrence of short circuit and providing high performance.

Specific examples of organic hole transport materials, to be contained in either a single-layer hole transport layer or a hole transport layer most distant from the second electrode 7 in a multi-layer transport layer, include the following materials, but are not limited thereto: oxadiazole compounds described in JP-34-5466-B; triphenylmethane compounds described in JP-45-555-B; pyrazoline compounds described in JP-52-4188-B; hydrazone compounds described in JP-55-42380-B; oxadiazole compounds described in JP-56-123544-A; tetraarylbenzidine compounds described in JP-54-58445-A; and stilbene compounds described in JP-58-65440-A and JP-60-98437-A.

Specific examples of the oxadiazole compounds include, but are not limited to, the following compound (21). Specific examples of the triphenylmethane compounds include, but are not limited to, the following compound (22). Specific examples of the pyrazoline compounds include, but are not limited to, the following compound (23). Specific examples of the hydrazone compounds include, but are not limited to, the following compound (24). Specific examples of the oxadiazole compounds include, but are not limited to, the following compound (25). Specific examples of the tetraarylbenzidine compounds include, but are not limited to, the following compound (26). Specific examples of the stilbene compounds include, but are not limited to, the following compounds (27) and (28).

(21)

(22)

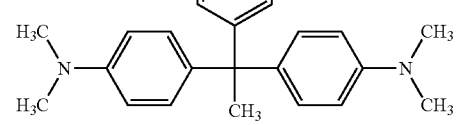
(23)

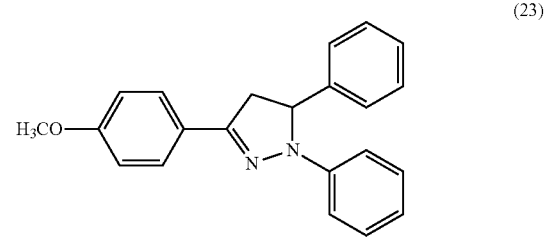
(24)

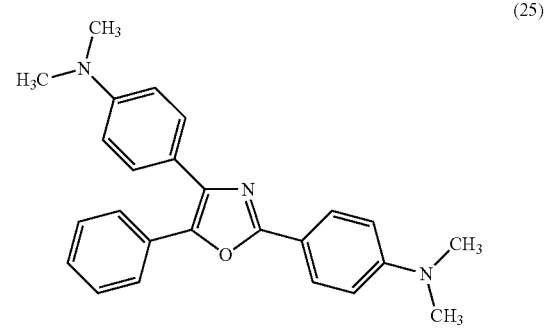
(25)

(26)
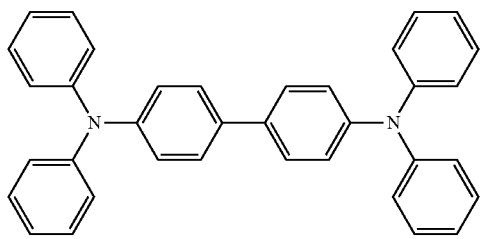

(27)
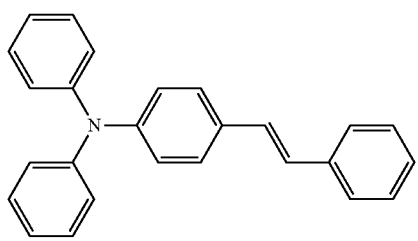

(28)
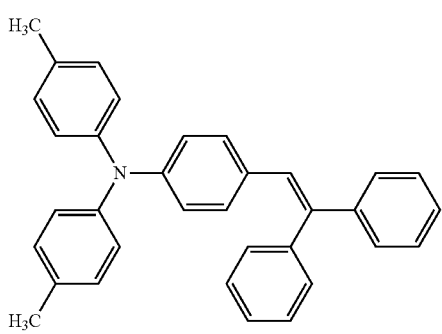

Formula (6)
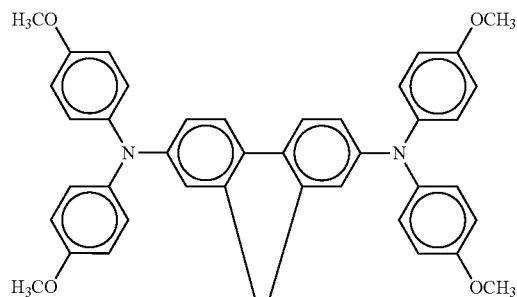

Formula (7)
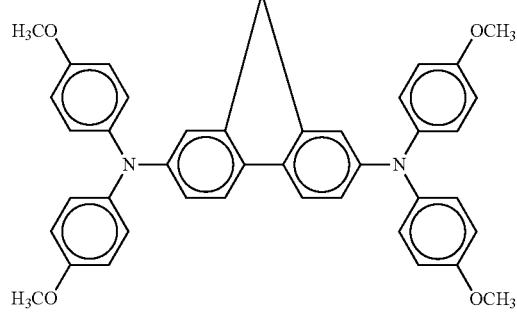

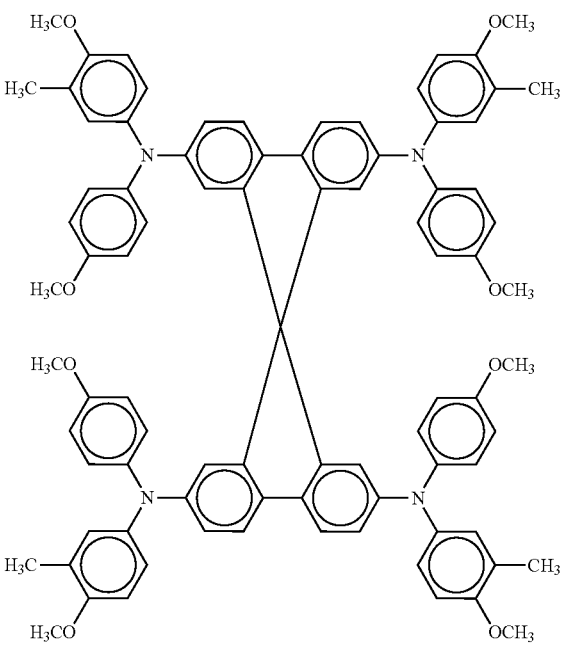

In particular, an organic hole transport material represented by the following formula (6) described in *J. Am. Chem. Soc.*, 133 (2011), 18042 and another organic hole transport material represented by the following formula (7) described in *J. Am. Chem. Soc.*, 135 (2013), 7378, each of which further represented by the general formula (2), exhibit distinctive photoelectric conversion characteristics.

Preferably, the content rate of the organic hole transport material represented by the general formula (2) in the single-layer hole transport layer or the hole transport layer most distant from the second electrode 7 in the multi-layer hole transport layer is in the range of from 50% to 95% by mass, and more preferably from 70% to 85% by mass.

Specific examples of the polymeric material contained in the hole transport layer closest to the second electrode 7 in the multi-layer hole transport layer include the following hole transport polymeric materials, but are not limited thereto:

polythiophene compounds such as poly(3-n-hexylthiophene), poly(3-n-octyloxythiophene), poly(9,9'-dioctylfluorene-co-bithiophene), poly(3,3'''-didodecyl-quarter-thiophene), poly(3,6-dioctylthieno[3,2-b]thiophene), poly(2,5-bis(3-decylthiophene-2-yl)thieno[3,2-b]thiophene), poly(3,4-didecylthiophene-co-thieno-[3,2-b]thiophene), poly(3,6-dioctylthieno[3,2-b]thiophene-co-thieno[3,2-b]thiophene), poly(3,6-dioctylthieno[3,2-b]thiophene-co-thiophene), and poly(3,6-dioctylthieno[3,2-b]thiophene-co-bithiophene); polyphenylenevinylene compounds such as poly[2-methoxy-5-(2-ethylhexyloxy)-1,4-phenylenevinylene], poly[2-methoxy-5-(3,7-dimethyloctyloxy)-1,4-phenylenevinylene], and poly[2-methoxy-5-(2-ethylphenyloxy)-1,4-phenylenevinylene)-co-(4,4'-biphenylene-vinylene); polyfluorene compounds such as poly(9,9'-didodecylfluorenyl-2,7-diyl), poly[(9,9-dioctyl-2,7-divinylenefluorene)-alt-co-(9,10-anthracene)], poly [(9,9-dioctyl-2,7-divinylenefluorene)-alt-co-(4,4'-biphenylene)], poly[(9,9-dioctyl-2,7-divinylenefluorene)-alt-co-(2-methoxy-5-(2-ethylhexyloxy)-1,4-phenylene)], and poly[(9,9-dioctyl-2,7-diyl)-co-(1,4-(2,5-dihexyloxy)benzene)]; polyphenylene compounds such as poly[2,5-dioctyloxy-1,4-phenylene] and poly[2,5-di(2-ethylhexyloxy-1,4-phenylene]; polyarylamine compounds such as poly[(9,9-dioctylfluorenyl-2,7-diyl)-alt-co-(N,N'-diphenyl)-N,N'-di(p-hexylphenyl)-1,4-diaminobenzene], poly[(9,9-dioctylfluorenyl-2,7-diyl)-alt-co-(N,N'-bis(4-octyloxyphenyl)benzidine-N,N'-(1,4-diphenylene)], poly[(N,N'-bis(4-octyloxyphenyl)benzidine-N,N'-(1,4-diphenylene)], poly[(N,N'-bis(4-(2-ethylhexyloxy)phenyl)benzidine-N,N'-(1,4-diphenylene)], poly[phenylimino-1,4-phenylenevinylene-2,5-dioctyloxy-1,4-phenylenevinylene-1,4-phenylene], poly[p-tolylimino-1,4-phenylenevinylene-2,5-di(2-ethylhexyloxy)-1,4-phenylenevinylene-1,4-phenylene], and poly[4-(2-ethylhexyloxy)phenylimino-1,4-biphenylene]; and polythiadiazole compounds such as poly[(9,9-dioctylfluorenyl-2,7-diyl)-alt-co-(1,4-benzo(2,1',3)thiadiazole] and poly (3,4-didecylthiophene-co-(1,4-benzo(2,1',3)thiadiazole).

Among these materials, polythiophene compounds and polyarylamine compounds are preferable in terms of carrier mobility and ionization potential.

An additive may be further added to the organic hole transport material.

Specific examples of the additive include, but are not limited to, iodine; metal iodides such as lithium iodide, sodium iodide, potassium iodide, cesium iodide, calcium iodide, copper iodide, iron iodide, and silver iodide; quaternary ammonium iodine salts such as tetraalkylammonium iodide and pyridinium iodide; metal bromides such as lithium bromide, sodium bromide, potassium bromide, cesium bromide, and calcium bromide; quaternary ammonium bromine salts such as tetraalkylammonium bromide and pyridinium bromide; metal chlorides such as copper chloride and silver chloride; metal salts of acetic acids such as copper acetate, silver acetate, and palladium acetate; metals salts of sulfuric acids such as copper sulfate and zinc sulfate; metal complexes such as ferrocyanic acid salt-ferricyanic acid salt, and ferrocene-ferricinium ion; sulfur compounds such as sodium polysulfide and alkyl thiol-alkyl disulfide; viologen dyes; hydroquinones; ionic liquids of imidazolium compounds described in Inorg. Chem., 35 (1996). 1168 such as 1,2-dimethyl-3-n-propylimidazolinium iodide, 1-methyl-3-n-hexylimidazolinium iodide, 1,2-dimethyl-3-ethylimidazolium trifluoromethane sulfonate, 1-methyl-3-butylimidazolium nonafluorobutyl sulfonate, 1-n-hexyl-3-methylimidazolinium bis(trifluoromethylsulfonyl)imide, and 1-methyl-3-ethylimidazolium bis(trifluoromethylsulfonyl)imide; basic compounds such as pyridine, 4-t-butyl pyridine, and benzimidazole; and lithium compounds such as lithium trifluoromethane sulfonylimide, lithium diisopropylimide, and lithium bis(trifluoromethanesulfonyl)imide.

Ionic liquids of imidazolium compounds can also be used. Specifically, 1-n-hexyl-3-methylimidazolinium bis(trifluoromethylsulfonyl)imide is preferable.

Since the hole transport layer contains the tertiary amine compound represented by the following general formula (1), the photoelectric conversion element according to an embodiment of the present invention can exhibit excellent photoelectric conversion characteristics even after being exposed to a high-temperature process.

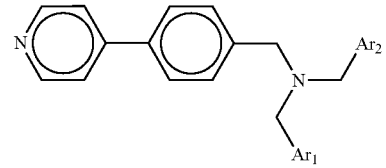

General Formula (1)

where each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring. The alkyl group and the alkoxy group may have a substituent. $Ar_1$ and $Ar_2$ may be either the same or different.

Tertiary butyl pyridine, that is one of basic compounds, is known as a liquid material having a relatively small molecular weight. A heat resistance test result of tertiary butyl pyridine performed at 60° C. has been reported (ACS Appl. Mater. Interfaces, 2015, 7(21), pp. 11107-11116). It has been generally considered that materials constituting the hole transport layer, such as an organic P-type semiconductor, a basic compound, and a lithium salt, are changed in morphology as the layer is exposed to a high-temperature process, resulting in a lowering of power.

One possible solution for suppressing the occurrence of morphology change involves increasing crystallinity of the organic P-type semiconductor. However, in solid-type dye sensitized solar cells, the organic P-type semiconductor can generate high power only when in an amorphous state. In view of this situation, the inventors of the present invention have found that the occurrence of morphology change can be suppressed by increasing the molecular weight of the basic compound. As a result, a solid-type dye sensitized solar cell that can generate high power is provided. This solar cell can increase both open circuit voltage and short circuit current density without deteriorating output even when being heated to a high temperature of about 120° C.

Preferably, the content of the tertiary amine compound represented by the general formula (1) in the hole transport layer is in the range of from 1 to 50 parts by mass, more preferably from 10 to 30 parts by mass, based on 100 parts by mass of the organic hole transport material.

As the hole transport layer contains the tertiary amine compound represented by the general formula (1), the photoelectric conversion element increases its internal resistance, thus reducing current loss under ultraweak light such as indoor light. The tertiary amine compound represented by the general formula (1) is an amine derivative having a tribenzyl backbone. This tertiary amine compound has a higher oxidation potential than the hole transport material represented by the general formula (2) and does not inhibit hole transportation. On the other hand, amine derivatives having an alkyl backbone have a lower oxidation potential and inhibit hole transportation. Those having two benzyl groups have weak basicity and poor solar cell power. As an amine derivative having a tribenzyl backbone, having high basicity and high oxidation potential that do not inhibit hole transport, is contained in the hole transport layer, the hole transport layer can acquire a proper degree of internal resistance.

For the purpose of improving conductivity, an oxidant may be added for converting a part of the organic hole transport material into radical cations.

Specific examples of the oxidant include, but are not limited to, tris(4-bromophenyl)aminium hexachloroantimonate, silver hexafluoroantimonate, nitrosonium tetrafluoroborate, silver nitrate, and cobalt complex compounds.

Not all the organic hole transport material need to be oxidized by the oxidant and only a part of them may be oxidized. The oxidant added to the system may be either taken out or kept therein.

The hole transport layer is directly formed on the porous electron transport layer 4 that is carrying the photosensitizing material. The hole transport layer is not limited in its formation method and can be formed by, for example, a vacuum film-forming method (e.g., vacuum deposition) or a wet film-forming method. In view of production cost, a wet film-forming method in which the porous electron transport layer is coated with a coating liquid is preferable.

In this wet film-forming method, how to apply the paste is not particularly limited. For example, the paste may be applied by means of dipping, spraying, wire bar, spin coating, roller coating, blade coating, gravure coating, or wet printing such as relief, offset, gravure, intaglio, rubber plate, and screen printings. Alternatively, the layer may be formed in a supercritical fluid or a subcritical fluid having lower temperature and pressure than the critical point.

The supercritical fluid is not limited in substance so long as it exists as a non-cohesive high-density fluid at temperatures and pressures beyond the region where gases and liquids can coexist (i.e., the critical point), without cohering even under compression, while having a temperature equal to or above the critical temperature and a pressure equal to or above the critical pressure. Specifically, those having a low critical temperature are preferable.

Specific examples of the supercritical fluid include, but are not limited to, carbon monoxide, carbon dioxide, ammonia, nitrogen, water, alcohol solvents (e.g., methanol, ethanol, n-butanol), hydrocarbon solvents (e.g., ethane, propane, 2,3-dimethylbutane, benzene, toluene), halogen solvents (e.g., methylene chloride, chlorotrifluoromethane), and ether solvents (e.g., dimethyl ether). Among these substances, carbon dioxide, having a supercritical pressure of 7.3 MPa and a supercritical temperature of 31° C., is preferable, because carbon dioxide is easy to put into a supercritical state and easy to handle owing to its non-combustibility.

Each of these fluids can be used alone or in combination with others.

The subcritical fluid is not limited in substance so long as it exists as a high-pressure liquid at temperatures and pressures near the critical point.

The above-described substances preferable for the supercritical fluid are also preferable for the subcritical fluid.

The supercritical fluid is not limited in critical temperature and critical pressure, but preferably has a critical temperature of from −273 to 300° C., more preferably from 0 to 200° C.

In addition, an organic solvent and/or entrainer can be used in combination with the supercritical fluid or subcritical fluid.

Addition of an organic solvent and/or entrainer facilitates adjustment of solubility in the supercritical fluid.

Specific examples of the organic solvent include, but are not limited to, ketone solvents such as acetone, methyl ethyl ketone, and methyl isobutyl ketone; ester solvents such as ethyl formate, ethyl acetate, and n-butyl acetate; ether solvents such as diisopropyl ether, dimethoxyethane, tetrahydrofuran, dioxolan, and dioxane; amide solvents such as N,N-dimethylformamide, N,N-dimethylacetamide, and N-methyl-2-pyrrolidone; halogenated hydrocarbon solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene.

After the hole transport layer has been formed on the electron transport layer covered with the photosensitizing material on the first electrode, the laminated body may be subjected to a press processing.

The press processing brings the organic hole transport material into a more intimate contact with the porous electrode, thus improving efficiency.

The press processing may be, for example, press molding using a flat plate such as an IR tablet pelletizer or a roll press method using a roller.

The pressure in the press processing is preferably 10 kgf/cm$^2$ or more and more preferably 30 kgf/cm$^2$ or more. The pressing time is preferably within 1 hour. Heat can be applied during the press processing, if necessary.

In the press processing, a release material may be sandwiched between the presser and the electrode.

Specific examples of the release material include, but are not limited to, fluorine resins such as polytetrafluoroethylene, polychlorotrifluoroethylene, tetrafluoroethylene-hexafluoropropylene copolymer, perfluoroalkoxyfluoro resin, polyvinylidene fluoride, ethylene-tetrafluoroethylene copolymer, ethylene-chlorotrifluoroethylene copolymer, and polyvinyl fluoride.

After the press processing and before provision of an opposite electrode, a metal oxide may be provided to between the organic hole transport layer and the second electrode. Specific examples of the metal oxide include, but are not limited to, molybdenum oxide, tungsten oxide, vanadium oxide, and nickel oxide. Among these materials, molybdenum oxide is preferable.

There is no limit on how to provide a metal oxide on the hole transport layer. For example, vacuum film-forming methods, such as sputtering and vacuum deposition, and wet film-forming methods can be employed.

Specifically, a wet film-forming method in which a paste dispersing a powder or sol of a metal oxide is applied to the hole transport layer is preferable.

In this wet film-forming method, how to apply the paste is not particularly limited.

For example, the paste may be applied by means of dipping, spraying, wire bar, spin coating, roller coating, blade coating, gravure coating, or wet printing such as relief, offset, gravure, intaglio, rubber plate, and screen printings. The film thickness is preferably in the range of from 0.1 to 50 nm and more preferably from 1 to 10 nm.

Second Electrode

The second electrode is formed on the hole transport layer or the metal oxide described above.

The second electrode may have a similar configuration to the first electrode. However, the substrate is not necessary so long as the strength and sealing performance are sufficiently secured.

Specific examples of usable materials for the second electrode include, but are not limited to, metals such as platinum, gold, silver, copper, and aluminum; carbon compounds such as graphite, fullerene, carbon nanotube, and graphene; conductive metal oxides such as ITO, FTO, and ATO; and conductive polymers such as polythiophene and polyaniline.

The second electrode is not limited in thickness. The second electrode may be formed of a single material or a mixture of two or more materials.

The second electrode can be formed on the hole transport layer by means of, for example, coating, lamination, vapor deposition, CVD (chemical vapor deposition), or bonding, depending on the types of materials constituting the second electrode and the hole transport layer.

In a case in which the second electrode is formed by a wet film-forming method using an organic solvent, the hole transport layer may be disadvantageously dissolved by the organic solvent. Thus, preferably, the second electrode is formed using an aqueous paste of a polythiophene derivative (e.g., PEDOT/PSS) or a metal nanowire. Since residual moisture will deteriorate the photoelectric conversion element, the element is heated to 100° C. or higher, preferably around 120° C., to remove moisture from the resulting layer.

When exposed to such a high-temperature process, conventional photoelectric conversion elements deteriorate. By contrast, the photoelectric conversion element according to an embodiment of the present invention exhibits excellent photoelectric conversion characteristics under ultraweak light such as indoor light even after being exposed to a high-temperature process.

To act as a photoelectric conversion element, at least one of the first electrode and the second electrode is substantively transparent.

According to an embodiment of the present invention, preferably, the first electrode is transparent to allow solar light to enter from the first electrode side. In this case, the second electrode is preferably made of a light reflective material such as metal-deposited or conductive-oxide-deposited glass or plastic, or a metallic thin film.

It is also effective to provide an antireflective layer on the solar light entering side.

The photoelectric conversion element according to a second embodiment of the present invention includes: a transparent conductive film substrate; a first electrode overlying the transparent conductive film substrate; a hole blocking layer overlying the first electrode; an electron transport layer overlying the hole blocking layer; an organic-inorganic perovskite compound layer overlying the electron transport layer; a hole transport layer overlying the organic-inorganic perovskite compound layer; and a second electrode overlying the hole transport layer. The hole transport layer contains the tertiary amine compound according to an embodiment of the present invention.

Figure 2:
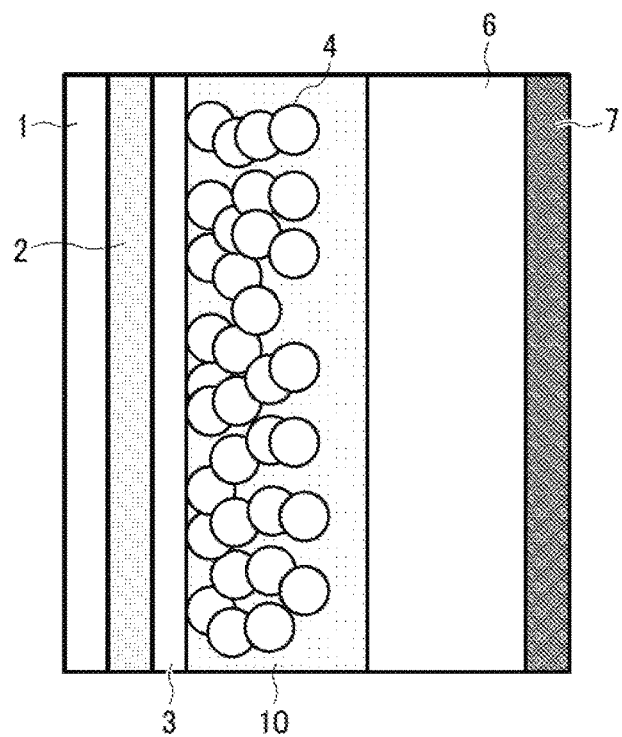
FIG. 2 is a cross-sectional view of a photoelectric conversion element according to another embodiment of the present invention.

A configuration of this photoelectric conversion element is described below with reference to FIG. 2. FIG. 2 is a cross-sectional view of a photoelectric conversion element according to the second embodiment of the present invention.

Referring to FIG. 2, a first electrode 2 is formed on a transparent conductive film substrate 1. A hole blocking layer 3 is formed on the first electrode 2. A porous electron transport layer 4 is formed on the hole blocking layer 3. An organic-inorganic perovskite compound layer 10 is formed on the porous electron transport layer 4. A hole transport layer 6 is formed on the organic-inorganic perovskite compound layer 10. A second electrode 7 is formed on the hole transport layer 6.

The first electrode, hole blocking layer, electron transport layer, hole transport layer, and second electrode illustrated in FIG. 2 according to the second embodiment are the same as those illustrated in FIG. 1 according to the first embodiment.

Organic-Inorganic Perovskite Compound Layer

The organic-inorganic perovskite compound layer 10 contains an organic-inorganic perovskite compound and is disposed on the electron transport layer.

The organic-inorganic perovskite compound is a composite material of an organic compound and an inorganic compound. Preferably, the organic-inorganic perovskite compound has a layered perovskite structure in which a layer made of a metal halide and another layer in which organic cation molecules are arranged are alternately laminated, and is represented by the following formula (a).

$$X_\alpha Y_\beta M_\gamma \qquad \text{Formula (a)}$$

In the formula (a), X represents a halogen atom, Y represents at least one of an alkylammonium, formamidinium, and cesium (excluding the case where Y represents cesium only), M represents at least one of lead and tin, and the ratio α/β/γ is 3/1/1.

More specifically, X represents a halogen atom such as chlorine, bromine, iodine, and a mixture thereof. Y represents at least one of an alkylammonium (such as methylammonium, ethylammonium, and n-butylammonium), formamidinium, and cesium. However, the case where Y represents cesium only is excluded. M represents lead and/or tin.

Preferably, the alkylammonium is methylammonium.

In a case in which each of X, Y, and M comprises two or more types of materials, each of α, β, and γ becomes the total of the materials.

The organic-inorganic perovskite compound may be produced by either a one-step deposition method or a two-step deposition method. The one-step deposition method may include the process of applying a solution or dispersion of a metal halide (e.g., a mixture of a lead halide and a tin halide), a halogenated alkylamine, and a halogenated formamidine onto the electron transport layer, followed by drying. The two-step deposition method may include the processes of applying a solution or dispersion of a metal halide onto the electron transport layer, followed by drying, and thereafter dipping it into a solution of a halogenated alkylamine or a halogenated formamidine. In particular, two-step deposition methods are more preferable. Preferably, the halogenated alkylamine is a halogenated methylamine. The organic-inorganic perovskite compound preferably includes at least one of a halogenated methylamine and a halogenated formamidine.

The solution or dispersion may be applied onto the electron transport layer by means of, for example, immersing, spin coating, spraying, dipping, roller, or air knife. Alternatively, the organic-inorganic perovskite compound may be deposited on the electron transport layer in a supercritical fluid such as carbon dioxide.

In the two-step deposition method, the metal halide deposited on the electron transport layer may be brought into contact with the solution of the halogenated alkylamine, etc., by means of, for example, immersing, spin coating, spraying, dipping, roller, or air knife. Alternatively, the organic-inorganic perovskite compound may be deposited by contacting the halogenated alkylamine in a supercritical fluid such as carbon dioxide.

Preferably, the organic-inorganic perovskite compound layer has a thickness of from 0.05 to 1 µm, more preferably from 0.1 to 0.5 µm.

After the organic-inorganic perovskite compound layer has been formed on the electron transport layer, a photosensitizing material can be adsorbed thereto. The photosensitizing material is not limited to a particular material so long as it can be photoexcited. Specific examples of such compounds include those exemplified in the first embodiment. The photosensitizing material can be adsorbed in the same manner as in the first embodiment. The organic-inorganic perovskite compound layer has hollow walls in between crystal structures. A solution of the photosensitizing material can permeate the layer to make the photosensitizing material adsorb to the surface of the porous electron transport layer.

The photoelectric conversion element according to an embodiment of the present invention may be sealed with a sealing material so as to prevent the element from deteriorating by oxygen, moisture, etc.

The sealing material and method are not limited to any particular material and method.

Use Application

The photoelectric conversion element according to an embodiment of the present invention is applicable to solar cells and power supply devices using the solar cells.

The photoelectric conversion element may be further applicable to conventional devices using a solar cell or a power supply device using the solar cell.

For example, the photoelectric conversion element can be applied to solar cells used in electronic desk calculators and wristwatches. In particular, the photoelectric conversion element according to an embodiment of the invention can be advantageously applied to power supply devices used in cell phones, electronic organizers, electronic papers, etc. In addition, the photoelectric conversion element can also be used as an auxiliary power supply for lengthening continuous operating time of charging-type or battery-type electronic devices. Furthermore, the photoelectric conversion element can be used as a substitute of a primary battery that is combined with a secondary battery, as a stand-alone power supply for sensors.

Synthesis Method of Tertiary Amine Compound

The tertiary amine compound according to an embodiment of the present invention can be easily synthesized by the following scheme as reported in *J. Org. Chem.*, 67(2002), 3029.

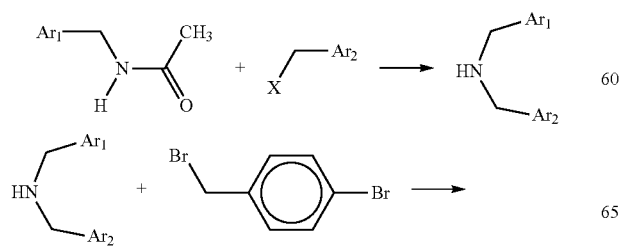

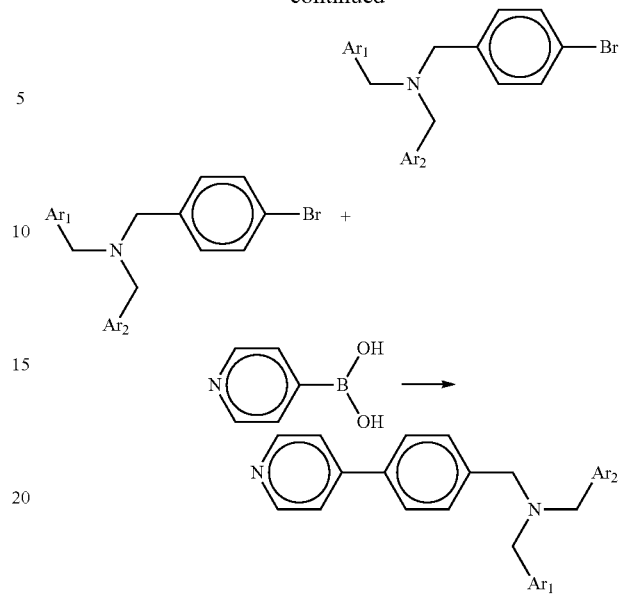

In the above scheme, each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring. The alkyl group and the alkoxy group may have a substituent. $Ar_1$ and $Ar_2$ may be either the same or different. X represents a halogen element.

EXAMPLES

Having generally described this invention, further understanding can be obtained by reference to certain specific examples which are provided herein for the purpose of illustration only and are not intended to be limiting.

Example I-1

Synthesis of Tertiary Amine Compound No. 1-1

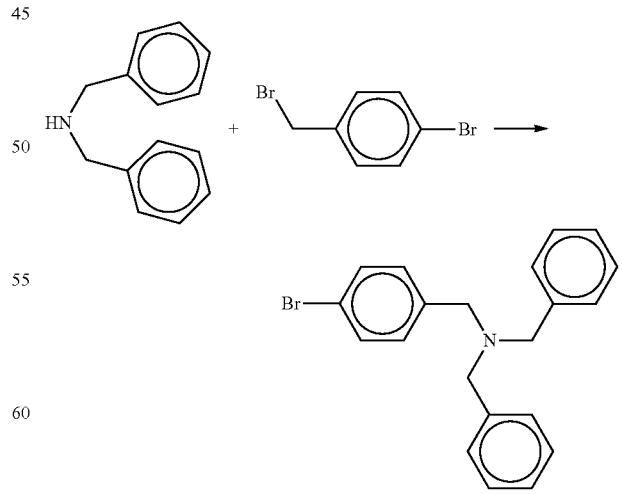

In a 50-ml three-neck flask, 4.99 g of 4-bromobenzylbromide (available from Tokyo Chemical Industry Co., Ltd.), 3.95 g of dibenzylamine (available from Tokyo Chemical Industry Co., Ltd.), and 4.14 g of potassium carbonate (available from Kanto Chemical Co., Inc.) were weighed and heat-stirred at 90° C. for 3 hours. The reaction product was extracted and mixed with magnesium sulfate, followed by filtration and condensation. The crude product was purified by column chromatography (toluene/cyclohexane=1/1). Thus, 7.08 g of a bromo intermediate in a colorless oil state was obtained.

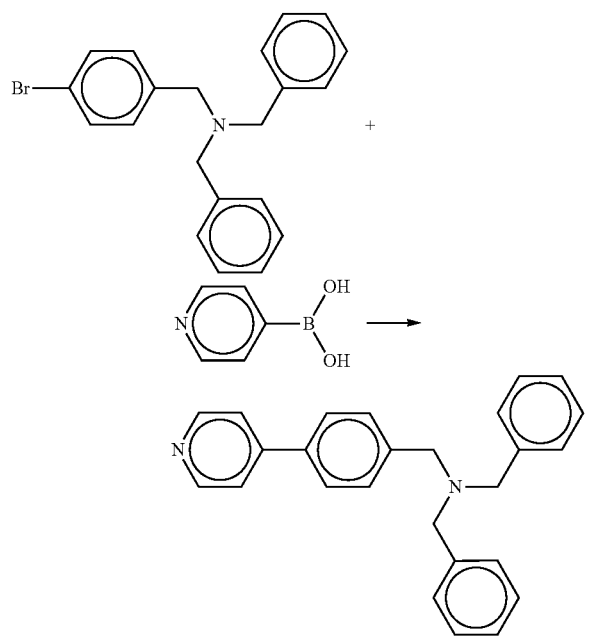

Figure 3:
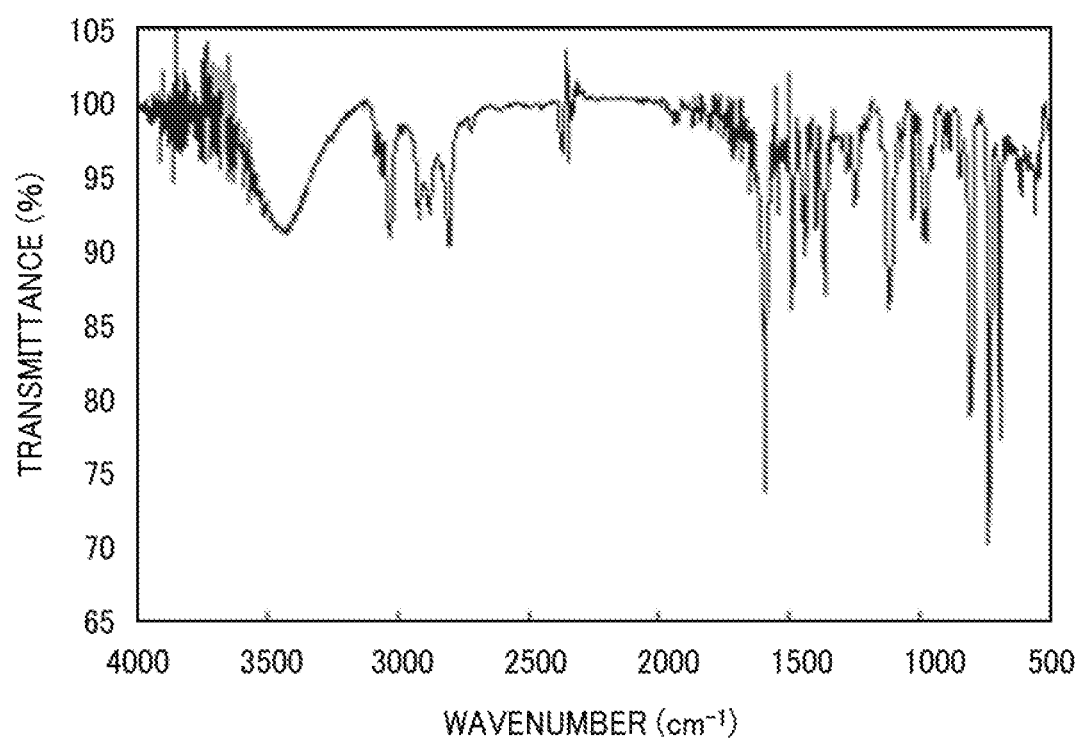
FIG. 3 is an IR (infrared) spectrum of a tertiary amine compound (Compound No. 1-1) used in Example I-1, according to an embodiment of the present invention.

Next, 5.9 g of the bromo intermediate synthesized above, 1.18 g of 4-pyridylboronic acid (available from Tokyo Chemical Industry Co., Ltd.), 0.93 g of tetrakis(triphenylphosphine)palladium (available from Tokyo Chemical Industry Co., Ltd.), 8.9 g of potassium carbonate (available from Kanto Chemical Co., Inc.), 100 ml of ethanol, and 100 ml of water were weighed and reflux-stirred under argon gas atmosphere. The reaction product was extracted and mixed with magnesium sulfate, followed by filtration and condensation. The crude product was purified by column chromatography (toluene/ethyl acetate=1/1). Thus, 1.3 g of a tertiary amine compound (Compound No. 1-1) in a colorless powder state was obtained. The IR spectrum of the obtained tertiary amine compound is shown in FIG. 3.

Example II-1

Preparation of Titanium Oxide Semiconductor Electrode

A dense hole blocking layer was formed with titanium oxide on an ITO glass substrate by reactive sputtering by oxygen gas using a titanium metal target.

Next, 3 g of titanium oxide (P90 available from Nippon Aerosil Co., Ltd.), 0.2 g of acetylacetone, and 0.3 g of a surfactant (polyoxyethylene octyl phenyl ether, available from Wako Pure Chemical Industries, Ltd.) were subjected to a bead mill treatment, along with 5.5 g of water and 1.0 g of ethanol, for 12 hours.

The resulting dispersion liquid was mixed with 1.2 g of a polyethylene glycol (#20,000) to prepare a paste.

The paste was applied onto the hole blocking layer to have a thickness of 1.5 μm, dried at room temperature, and then burnt in the air at 500° C. for 30 minutes, thus forming a porous electron transport layer.

Preparation of Photoelectric Conversion Element

The titanium oxide semiconductor electrode prepared above was dipped in a 0.5 mM acetonitrile/t-butanol (1/1 by volume) solution of a photosensitizing material D102 (available from Mitsubishi Paper Mills Limited) represented by the formula (4) and left at rest for 1 hour in a dark place, so that the photosensitizing material was adsorbed thereto.

Next, the semiconductor electrode carrying the photosensitizing material was coated with a solution prepared by mixing 12.83 mg of lithium bis(trifluoromethanesulfonyl)imide (available from Kanto Chemical Co., Inc.) and 36.66 mg of the tertiary amine compound represented by the general formula (1) (Compound No. 1-1) into 1 ml of a chlorobenzene solution of 183.3 mg of an organic hole transport material represented by the following formula (8) (H101 available from Dyesol Ltd.) by spin coating, thus forming a hole transport layer. Further, a paste of PEDOT/PSS (ORGACON EL-P-5015 available from Sigma-Aldrich) was further applied onto the hole transport layer by screen printing and dried at 120° C. for 30 minutes, thus forming a second electrode. Thus, a photoelectric conversion element was prepared.

Formula (8)

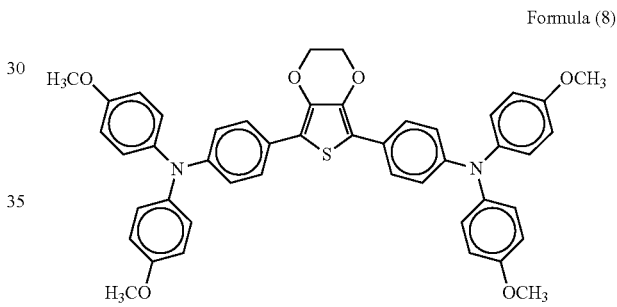

Evaluation of Photoelectric Conversion Element

The photoelectric conversion element prepared above was subjected to a measurement of photoelectric conversion efficiency under white LED light irradiation (100 lux, 25 μW/cm$^2$). The used white LED was a desk lamp CDS-90α (in Study Mode) available from Cosmotechno Co., Ltd. The used tester was a solar cell evaluating system As-510-PV03 available from NF Corporation. The evaluation results are shown in Table 1.

Example II-2

The procedure in Example II-1 was repeated except for replacing the organic hole transport material with another organic hole transport material represented by the formula (6) (SHT-263 available from Merk KGaA), further represented by the general formula (2). The evaluation results are shown in Table 1.

Example II-3

The procedure in Example II-1 was repeated except for replacing the organic hole transport material with another organic hole transport material represented by the formula (7) (LT-S9170 available from Luminescence Technology Corp.), further represented by the general formula (2). The evaluation results are shown in Table 1.

Examples II-4 to II-7

The procedure in Example II-3 was repeated except for replacing the tertiary amine compound (Compound No. 1-1) with another tertiary amine compound as described in Table 1. The evaluation results are shown in Table 1.

Example II-8

The procedure in Example II-2 was repeated except for replacing the second electrode with a silver film having a thickness of 100 nm formed by vacuum deposition. The evaluation results are shown in Table 1.

Example III-1

Preparation of Titanium Oxide Semiconductor Electrode

First, 2 ml of titanium tetra-n-propoxide, 4 ml of acetic acid, 1 ml of ion-exchange water, and 40 ml of 2-propanol were mixed. The mixture liquid was applied onto a FTO glass substrate by spin coating, dried at room temperature, and burnt in the air at 450° C. for 30 minutes. The same mixture liquid was reapplied onto the above-obtained electrode by spin coating to have a thickness of 50 nm and thereafter burnt in the air at 450° C. for 30 minutes, thus forming a dense hole blocking layer.

A titanium oxide paste (18NR-T available from Dyesol Ltd.) was applied onto the hole blocking layer by spin coating to have a thickness of 300 nm, dried by hot air at 120° C. for 3 minutes, and then burnt in the air at 500° C. for 30 minutes, thus forming a porous electron transport layer.

Preparation of Organic-Inorganic Perovskite Compound Layer

A solution in which 0.461 g of lead (II) iodide (available from Tokyo Chemical Industry Co., Ltd.) and 0.159 g of methylamine iodide (available from Tokyo Chemical Industry Co., Ltd.) were dissolved in 1 ml of N,N-dimethylformamide (available from Kanto Chemical Co., Inc.) was applied onto the above-prepared porous titanium oxide electrode by spin coating and dried at 120° C. for 10 minutes. Thus, an organic-inorganic perovskite compound layer containing $CH_3NH_3PBI_3$ was prepared.

Preparation of Hole Transport Layer

A chlorobenzene solution dissolving 60 mM of the organic hole transport material represented by the formula (6) (SHT-263 available from Merk KGaA), 14 mM of lithium bis(trifluoromethanesulfonyl)imide (available from Kanto Chemical Co., Inc.), and 53 mM of the tertiary amine compound (Compound No. 1-1) represented by the general formula (1) was formed into a film by spin coating and dried naturally. Further, a gold film having a thickness of about 100 nm was formed thereon by vacuum vapor deposition. Thus, a solar cell element was prepared.

Evaluation of Photoelectric Conversion Element

The photoelectric conversion element prepared above was subjected to a measurement of photoelectric conversion efficiency under white LED light irradiation (1,000 lux, 250 $\mu W/cm^2$). The used white LED was a desk lamp CDS-90a (in Study Mode) available from Cosmotechno Co., Ltd. The used tester was a solar cell evaluating system As-510-PV03 available from NF Corporation.

As a result, the open voltage was 0.68 V, the short-circuit current density was 140.2 $\mu A/cm^2$, the fill factor was 0.69, and the maximum output was 65.78 $\mu W/cm^2$, which are good values.

Example III-2

The procedure in Example III-1 was repeated except for replacing the tertiary amine compound (Compound No. 1-1) with another tertiary amine compound (Compound No. 1-5). As a result, the open voltage was 0.67 V, the short-circuit current density was 145.2 $\mu A/cm^2$, the fill factor was 0.67, and the maximum output was 65.18 $\mu W/cm^2$, which are good values.

Example III-3

After the outer periphery had been sealed with an epoxy resin and glass, the photoelectric conversion element prepared in Example III-1 was put in an oven at 60° C. for 100 hours.

After this endurance test at 60° C. for 100 hours, the photoelectric conversion element was subjected to the evaluations in the same manner as in Example III-1. As a result, the open voltage was 0.62 V, the short-circuit current density was 146.6 $\mu A/cm^2$, the fill factor was 0.68, and the maximum output was 61.80 $\mu W/cm^2$, which are good values.

The maximum output retention rate after the endurance test was 93.9% based on the initial value (i.e., the maximum output of the photoelectric conversion element prepared in Example III-1), which indicates good durability.

Example III-4

After the outer periphery had been sealed with an epoxy resin and glass, the photoelectric conversion element prepared in Example III-2 was put in an oven at 60° C. for 100 hours.

After this endurance test at 60° C. for 100 hours, the photoelectric conversion element was subjected to the evaluations in the same manner as in Example III-1.

As a result, the open voltage was 0.63 V, the short-circuit current density was 148.2 $\mu A/cm^2$, the fill factor was 0.66, and the maximum output was 61.62 $\mu W/cm^2$, which are good values.

The maximum output retention rate after the endurance test was 94.5% based on the initial value (i.e., the maximum output of the photoelectric conversion element prepared in Example III-2), which indicates good durability.

Example III-5

The procedure in Example III-1 was repeated except for replacing the 0.461 g of lead (II) iodide (available from Tokyo Chemical Industry Co., Ltd.) with a mixture of 0.415 g of lead (II) iodide (available from Tokyo Chemical Industry Co., Ltd.) and 0.037 g of tin (II) iodide (available from Alfa Aesar).

As a result, the open voltage was 0.57 V, the short-circuit current density was 155.2 $\mu A/cm^2$, the fill factor was 0.65, and the maximum output was 57.50 $\mu W/cm^2$, which are good values, although slightly lower than those values for the case in which lead iodide was used alone.

Example III-6

The procedure in Example III-1 was repeated except for replacing the 0.461 g of lead (II) iodide (available from Tokyo Chemical Industry Co., Ltd.) with a mixture of 0.369 g of lead (II) iodide (available from Tokyo Chemical Industry Co., Ltd.) and 0.075 g of tin (II) iodide (available from Alfa Aesar).

As a result, the open voltage was 0.54 V, the short-circuit current density was 157.7 µA/cm², the fill factor was 0.64, and the maximum output was 54.50 µW/cm², which are good values, although slightly lower than those values for the case in which lead iodide was used alone.

Example III-7

The procedure in Example III-1 was repeated except for replacing the 0.159 g of methylamine iodide (available from Tokyo Chemical Industry Co., Ltd.) with a mixture of 0.135 g of methylamine iodide (available from Tokyo Chemical Industry Co., Ltd.) and 0.024 g of formamidine iodide (available from Tokyo Chemical Industry Co., Ltd.).

As a result, the open voltage was 0.65 V, the short-circuit current density was 140.4 µA/cm², the fill factor was 0.70, and the maximum output was 63.88 µW/cm², which are good values.

Example III-8

The procedure in Example III-1 was repeated except for replacing the 0.159 g of methylamine iodide (available from Tokyo Chemical Industry Co., Ltd.) with a mixture of 0.135 g of methylamine iodide (available from Tokyo Chemical Industry Co., Ltd.), 0.017 g of formamidine iodide (available from Tokyo Chemical Industry Co., Ltd.), and 0.013 g of cesium iodide (available from Sigma-Aldrich).

As a result, the open voltage was 0.64 V, the short-circuit current density was 142.1 µA/cm², the fill factor was 0.69, and the maximum output was 62.75 µW/cm², which are good values.

Example III-9

The procedure in Example III-1 was repeated except for replacing the 0.159 g of methylamine iodide (available from Tokyo Chemical Industry Co., Ltd.) with a mixture of 0.143 g of methylamine iodide (available from Tokyo Chemical Industry Co., Ltd.) and 0.026 g of cesium iodide (available from Sigma-Aldrich).

As a result, the open voltage was 0.62 V, the short-circuit current density was 139.1 µA/cm², the fill factor was 0.69, and the maximum output was 59.51 µW/cm², which are good values.

Comparative Example 1

The procedure in Example II-2 was repeated except for replacing the tertiary amine compound (Compound No. 1-1) with tertiary butyl pyridine (tBP available from Sigma-Aldrich). The evaluation results are shown in Table 1.

Comparative Example 2

The procedure in Example II-2 was repeated except for replacing the tertiary amine compound (Compound No. 1-1) with the following compound (DBAP). The evaluation results are shown in Table 1.

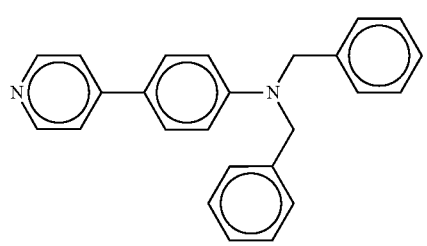

Comparative Example 3

The procedure in Example II-8 was repeated except for replacing the tertiary amine compound (Compound No. 1-1) with tertiary butyl pyridine (tBP available from Sigma-Aldrich). The evaluation results are shown in Table 1.

Comparative Example 4

The procedure in Example III-1 was repeated except for replacing the tertiary amine compound (Compound No. 1-1) with tertiary butyl pyridine (tBP available from Sigma-Aldrich).

As a result, the open voltage was 0.52 V, the short-circuit current density was 102.2 µA/cm², the fill factor was 0.66, and the maximum output was 35.07 µW/cm².

Comparative Example 5

The procedure in Example III-1 was repeated except for replacing the tertiary amine compound (Compound No. 1-1) with the compound (DBAP) described above.

As a result, the open voltage was 0.58 V, the short-circuit current density was 115.4 µA/cm², the fill factor was 0.67, and the maximum output was 44.84 µW/cm².

Comparative Example 6

After the outer periphery had been sealed with an epoxy resin and glass, the photoelectric conversion element prepared in Comparative Example 4 was put in an oven at 60° C. for 100 hours.

After this endurance test at 60° C. for 100 hours, the photoelectric conversion element was subjected to the evaluations in the same manner as in Example III-1.

As a result, the open voltage was 0.43 V, the short-circuit current density was 95.5 µA/cm², the fill factor was 0.57, and the maximum output was 23.04 µW/cm².

The maximum output retention rate after the endurance test was 65.7% based on the initial value (i.e., the maximum output of the photoelectric conversion element prepared in Comparative Example 4).

Comparative Example 7

After the outer periphery had been sealed with an epoxy resin and glass, the photoelectric conversion element prepared in Comparative Example 5 was put in an oven at 60° C. for 100 hours.

After this endurance test at 60° C. for 100 hours, the photoelectric conversion element was subjected to the evaluations in the same manner as in Example III-1.

As a result, the open voltage was 0.49 V, the short-circuit current density was 103.3 µA/cm², the fill factor was 0.61, and the maximum output was 30.87 µW/cm².

The maximum output retention rate after the endurance test was 68.8% based on the initial value (i.e., the maximum output of the photoelectric conversion element prepared in Comparative Example 5).

TABLE 1

| No. | Organic Hole Transport Material | Basic Compound | Second Electrode | Short-circuit Current Density ($\mu A/cm^2$) | Open Voltage (V) | Fill Factor | Maximum Output ($\mu W/cm^2$) |
|---|---|---|---|---|---|---|---|
| Example II-1 | H101 | No. 1-1 | PEDOT/PSS | 9.71 | 0.69 | 0.79 | 5.29 |
| Example II-2 | SHT-263 | | | 9.85 | 0.71 | 0.78 | 5.45 |
| Example II-3 | LT-S9170 | | | 9.96 | 0.72 | 0.78 | 5.59 |
| Example II-4 | | No. 1-2 | | 9.91 | 0.73 | 0.78 | 5.64 |
| Example II-5 | | No. 1-5 | | 10.25 | 0.74 | 0.76 | 5.76 |
| Example II-6 | | No. 1-7 | | 10.06 | 0.73 | 0.77 | 5.65 |
| Example II-7 | | No. 1-8 | | 10.51 | 0.72 | 0.78 | 5.90 |
| Example II-8 | SHT-263 | No. 1-1 | Ag | 7.89 | 0.67 | 0.77 | 4.07 |
| Comparative Example 1 | SHT-263 | tBP | PEDOT/PSS | 4.76 | 0.59 | 0.72 | 2.02 |
| Comparative Example 2 | | DBAP | | 3.98 | 0.51 | 0.71 | 1.44 |
| Comparative Example 3 | | tBP | Ag | 5.87 | 0.65 | 0.76 | 2.90 |

TABLE 2

| No. | Organic-Inorganic Perovskite Compound X | Y | M | Basic Compound | Endurance Test | Short-circuit Current Density ($\mu A/cm^2$) | Open Voltage (V) | Fill Factor | Maximum Output ($\mu W/cm^2$) |
|---|---|---|---|---|---|---|---|---|---|
| Example III-1 | I | $CH_3NH_3$ | Pb | No. 1-1 | No | 140.2 | 0.68 | 0.69 | 65.78 |
| Example III-2 | I | $CH_3NH_3$ | Pb | No. 1-5 | No | 145.2 | 0.67 | 0.67 | 65.18 |
| Example III-3 | I | $CH_3NH_3$ | Pb | No. 1-1 | Yes | 146.6 | 0.62 | 0.68 | 61.80 |
| Example III-4 | I | $CH_3NH_3$ | Pb | No. 1-5 | Yes | 148.2 | 0.63 | 0.66 | 61.62 |
| Example III-5 | I | $CH_3NH_3$ | Pb:Sn = 0.9:0.1 | No. 1-1 | No | 155.2 | 0.57 | 0.65 | 57.50 |
| Example III-6 | I | $CH_3NH_3$ | Pb:Sn = 0.8:0.2 | No. 1-1 | No | 157.7 | 0.54 | 0.64 | 54.50 |
| Example III-7 | I | $CH_3NH_3$:$NHCHNH_2$ = 0.85:0.15 | Pb | No. 1-1 | No | 140.4 | 0.65 | 0.70 | 63.88 |
| Example III-8 | I | $CH_3NH_3$:$NHCHNH_2$:Cs = 0.85:0.10:0.05 | Pb | No. 1-1 | No | 142.1 | 0.64 | 0.69 | 62.75 |
| Example III-9 | I | $CH_3NH_3$:Cs = 0.9:0.1 | Pb | No. 1-1 | No | 139.1 | 0.62 | 0.69 | 59.51 |
| Comparative Example 4 | I | $CH_3NH_3$ | Pb | tBP | No | 102.2 | 0.52 | 0.66 | 35.07 |
| Comparative Example 5 | I | $CH_3NH_3$ | Pb | DBAP | No | 115.4 | 0.58 | 0.67 | 44.84 |
| Comparative Example 6 | I | $CH_3NH_3$ | Pb | tBP | Yes | 95.5 | 0.43 | 0.57 | 23.04 |
| Comparative Example 7 | I | $CH_3NH_3$ | Pb | DBAP | Yes | 103.3 | 0.49 | 0.61 | 30.87 |

In Examples, II-1 to II-7, each photoelectric conversion element was subjected to heat drying in the process of preparing the second electrode. Thus, the short-circuit current density and open voltage were increased and the output was specifically improved in Examples II-1 to II-7 compared to Example II-8 in which heat drying was not conducted. In Comparative Examples 1 and 3 in each of which tertiary butyl pyridine (tBP) was used, it is confirmed that the output was lowered by the heat, as is the case of conventional photoelectric conversion elements. In Comparative Example 2 in which DBAP (a tertiary amine compound having two benzyl groups) was used, it is confirmed that the internal resistance was lowered and the output was lowered because the basicity of DBPA is slightly weak.

In Examples III-1 to III-10, initial properties of each photoelectric conversion element, such as the open voltage, short-circuit current density, fill factor, and maximum output, are better than those in Comparative Examples 4 to 7. In addition, the maximum output retention rate after the endurance test and high-temperature storage durability are also better in Example III-1 to III-10 compared to Comparative Examples 4 to 7.

It is clear from these results that the photoelectric conversion elements according to some embodiments of the present invention exhibit excellent photoelectric conversion characteristics in ultraweak light environments. Furthermore, the photoelectric conversion elements according to some embodiments of the present invention gain higher power by being exposed to a high-temperature process that is generally employed in a low-cost manufacturing process.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. A photoelectric conversion element comprising:
a first electrode;
a hole blocking layer;
an electron transport layer;
a hole transport layer; and
a second electrode, wherein the hole transport layer comprises a tertiary amine compound represented by formula (1):

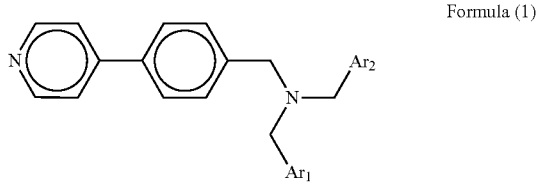

Formula (1)

where each of $Ar_1$ and $Ar_2$ independently represents a benzene ring having an alkyl group or an alkoxy group, an unsubstituted benzene ring, a naphthalene ring having an alkyl group or an alkoxy group, or an unsubstituted naphthalene ring.

2. The photoelectric conversion element of claim 1, wherein the hole transport layer contains a hole transport material represented by formula (2):

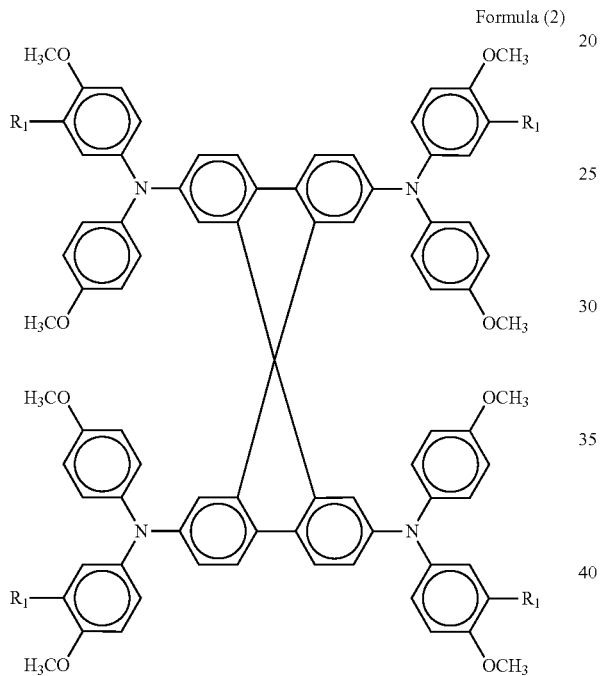

Formula (2)

where $R_1$ represents a hydrogen atom or methyl group.

3. The photoelectric conversion element of claim 1, wherein the electron transport layer contains titanium oxide.

4. The photoelectric conversion element of claim 1, wherein the hole blocking layer contains titanium oxide.

5. The photoelectric conversion element of claim 1 further comprising:

a transparent conductive film substrate;

an organic-inorganic perovskite compound layer, wherein the first electrode overlays the transparent conductive film substrate, the hole blocking layer overlays the first electrode, the electron transport layer overlays the hole blocking layer, the organic-inorganic perovskite compound layer overlays the electron transport layer, the hole transport layer overlays the organic-inorganic perovskite compound layer, and the second electrode overlays the hole transport layer.

6. The photoelectric conversion element of claim 5, wherein the organic-inorganic perovskite compound layer contains an organic-inorganic perovskite compound represented by formula (a):

$$X_\alpha Y_\beta M_\gamma \qquad \text{Formula (a)}$$

where X represents a halogen atom; Y represents at least one of an alkylammonium, formamidinium, and cesium, excluding the case where Y represents cesium only; M represents at least one of lead and tin; and the ratio $\alpha/\beta/\gamma$ is 3/1/1.

7. The photoelectric conversion element of claim 6, wherein the alkylammonium includes methylammonium.

8. A solar cell comprising the photoelectric conversion element of claim 1.

9. A solar cell comprising the photoelectric conversion element of claim 5.

* * * * *